United States Patent
Nishida et al.

(10) Patent No.: US 6,633,376 B1
(45) Date of Patent: Oct. 14, 2003

(54) APPARATUS FOR INSPECTING A PRINTED CIRCUIT BOARD

(75) Inventors: Satoshi Nishida, Tokyo (JP); Masanori Mizuno, Tokyo (JP); Miki Kurosawa, Tokyo (JP); Shozui Takeno, Tokyo (JP); Masaharu Moriyasu, Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/719,610
(22) PCT Filed: Aug. 10, 1998
(86) PCT No.: PCT/JP98/03546
§ 371 (c)(1),
(2), (4) Date: Dec. 12, 2000
(87) PCT Pub. No.: WO00/09993
PCT Pub. Date: Feb. 24, 2000

(51) Int. Cl.[7] .................................................. G01N 21/58
(52) U.S. Cl. .................................................... 356/237.5
(58) Field of Search .......................... 356/237.4, 237.5, 356/237.6, 241.1; 348/126; 382/147

(56) References Cited

U.S. PATENT DOCUMENTS 4,152,723 A * 5/1979 McMahon et al. ........ 250/458.1
4,816,686 A * 3/1989 Hara et al. ................ 356/237.5

FOREIGN PATENT DOCUMENTS

| JP | A 2-69640 | 3/1990 |
|----|-----------|--------|
| JP | A 5-152400 | 6/1993 |
| JP | A 5-312552 | 12/1993 |
| JP | A 5-322795 | 12/1993 |
| JP | A 6-18427 | 1/1994 |
| JP | A-6-102191 | 4/1994 |
| JP | A-6-118012 | 4/1994 |
| JP | A 7-43123 | 2/1995 |
| JP | A 7-83841 | 3/1995 |
| JP | A-8-122265 | 5/1996 |
| JP | A 7-22483 | 1/1998 |

* cited by examiner

Primary Examiner—Richard A. Rosenberger
(74) Attorney, Agent, or Firm—Sughrue Mion, PLLC

(57) ABSTRACT

As a scanning device for positioning the irradiation position of the laser beam emitted from a laser oscillator at a position of arbitrary coordinates in the commanded mutually orthogonal X-axis direction and Y-axis direction, two galvanomirrors having mutually orthogonal rotary axes and a scan lens are provided, and the light generated from a printed circuit board irradiated with laser beam is detected by a detector, and approval or rejection of inspection result at each position of coordinates is judged on the basis of the output signal of the detector.

21 Claims, 21 Drawing Sheets

(a) (b)

(a) (b)

(a)

(b)

(a)

(b)

APPARATUS FOR INSPECTING A PRINTED CIRCUIT BOARD

TECHNICAL FIELD

The present invention relates to an apparatus for inspecting a printed circuit board using laser beam. More particularly, this invention relaters to an apparatus for detecting unremoved material remaining in the bottom of blind via hole or processed groove provided in a laminated printed wiring board, or measuring the thickness, optically, using laser beam.

BACKGROUND ART

Along with the recent advancement in performance of electronic appliances, higher density of wiring is being demanded. To satisfy this demand, the printed circuit board is laminated in multiple layers and down-sized.

A laminated printed wiring board requires formation of ultra-fine stop holes for conduction and connection between layers. These holes have a diameter of about 150 $\mu$m and are called blind via hole (BVH). With present day technology, it is difficult to drill holes or process stop holes of ø0.2 mm or less. Furthermore, the thickness of the insulating layer is generally less than 100 $\mu$m in a high density printed circuit board, and depth control is difficult in such thin layer. accordingly, it is impossible to form ultra-fine BVH by drilling.

A method using laser beam is being noticed as a BVH forming method replacing the drilling process. This processing method makes use of the difference in the absorption of light energy in the insulating material for forming the printed circuit board such as resin and glass fiber, and in the conductive layer which is made of copper.

As the light source of laser beam, carbon dioxide laser is partly put in use, because, copper reflects carbon dioxide laser almost completely. As shown in FIG. 22(a), a copper foil removal part b of desired diameter is formed at a specified position of copper foil a by etching or the like. Then, and by irradiating this copper foil removal part b with laser beam L, the insulating substrate part c of resin or glass fiber is decomposed and removed. Thus, an ultra-fine hole d is formed as shown in FIG. 22(b).

As shown in FIG. 23, moreover, a copper foil e may be previously laminated inside of the hole processing part (inside of the insulating substrate). Accordingly, decomposition and removal of the insulating member stops at this copper foil e, so that a stop hole f stopping securely at the copper foil e can be formed.

However, as shown in FIG. 23, if the stop hole f stopping at the copper foil e is machined using carbon dioxide laser, even if the laser beam is sufficiently emitted, the resin of the insulating member of thickness of 1 $\mu$m or less is left over on the copper foil e. This remaining resin after must be removed completely in a later process by etching with permanganic acid or the like.

Some times these holes are very small in diameter. Therefore, the etchant hardly goes inside the hole. If the thickness of the residual resin exceeds 1 $\mu$m due to defective laser machining condition or the like, then the residual resin may not be removed completely in some holes. If the BVH is formed by plating in this state, the resin is partly remaining between the plating film and the inner layer copper foil, and if stress is applied by heat cycle or the like, the plating film may be peeled off from the portion of the residual resin.

Accordingly, it is required to inspect the thickness of the residual resin of the stop hole after laser machining.

As an apparatus for such inspection, an optical microscope as shown in FIG. 24 is used. In this inspection apparatus, white light from a light source 100 is emitted to a printed circuit board W through an objective lens 102 from a beam splitter 101. The light reflected from the printed circuit board W is magnified by the objective lens 102, and an inverted real image Ea is formed ahead of a focusing lens 103, and its real image Eb is taken by a CCD camera 104.

When the white light is emitted to the surface of the residual resin, it is partly reflected, but the rest passes through the residual resin to reach the copper foil in the bottom. This light that falls on the copper layer is reflected therefrom. Therefore, when white light is emitted to the thin resin layer on the copper foil as illuminating light, the majority of reflected light returns from the copper foil. Thus, it is hard to discriminate the presence of residual resin.

Accordingly, in the inspection apparatus using optical microscope, although a residual resin of more than 10 $\mu$m may be detected, the precision of detection is poor as for residual resin of about several $\mu$m. Thus, this apparatus is not suited to inspection in mass production line, but can only be used to inspect the thickness of the residual resin after cutting and grinding the processing part after plating and observing the section. Further, this apparatus takes too much time in inspection, and all pieces cannot be inspected.

An optical inspection apparatus that uses ultraviolet laser beam is disclosed in Japanese Patent Application Laid-Open No. 7-83841. This optical inspection apparatus comprises, as shown in FIG. 25, an ultraviolet laser source 200, a collimator lens 201, a mirror 202, a beam splitter 203, a motor-driven rotating polyhedral mirror 204, a scan lens 205, a re-focusing lens 206, a pin hole member 207, and a photomultiplier 208.

In this optical inspection apparatus, the laser beam generated by the ultraviolet laser source is magnified by the collimator lens 201, the magnified laser beam is guided into the rotating polyhedral mirror 46 by way of the mirror 202 and beam splitter 203, and it is scanned by the rotating scanning mirror 46 and focused on the printed circuit board W to be inspected by the scan lens 205.

The ultraviolet ray generated from the printed circuit board W by irradiation with laser beam is returned recursively in the reverse route of the incident route, and is guided into the retroreflection detecting system by the beam splitter 203 disposed in the optical path. This ultraviolet reflected light is focused by the re-focusing lens 206. On the focusing plane of the re-focusing lens 206, the image near the irradiation point of the laser beam of the printed circuit board W to be inspected is observed. By the pin hole member 207 disposed on this focusing plane, only the central part is separated, and detected by the photomultiplier 208.

This optical inspection apparatus inspects by scanning over the entire printed circuit board to detect the stop holes and grooves. Accordingly, it takes time. This problem arises because the rotating polyhedral mirror is used, and the laser beam cannot be brought up to the commanded position.

Besides, because the inspection makes use of the reflected light, the inspection result may vary depending on the inclination of the printed circuit board to be inspected. Furthermore, since the reflected light is detected by disposing a mask (pin hole member) on the focusing plane and extracting the light in its central part, the luminance is too low and reliable detection of residual resin is difficult.

The invention is devised to solve these problems, and it is hence an object thereof to present an apparatus for inspecting a printed circuit board of high reliability capable of detecting the residual resin on a copper foil nondestructively, securely, and at high precision and high speed, and moreover an inspection apparatus of printed circuit board having a re-processing function for re-removing the unremoved material.

DISCLOSURE OF THE INVENTION

The invention presents an apparatus for inspecting printed circuit board. This apparatus comprises a laser oscillator, a scanning device for positioning the irradiation position of laser beam emitted from the laser oscillator to a position of arbitrary coordinates in the mutually orthogonal X-axis direction and Y-axis direction being commanded, and a detector for detecting the light generated from the printed circuit board irradiated with the laser beam.

Therefore, the position of arbitrary coordinates commanding the irradiation position of laser beam can be instantly set by the scanning device.

Further, in this inspection apparatus, the scanning device is composed by combination of two galvanomirrors having mutually orthogonal rotary shafts, and a scan lens.

Therefore, the irradiation position of laser beam is set at high precision by the combination of two galvanomirrors and scan lens.

Further, this inspection apparatus further comprises a controller for storing the position of coordinates for processing stop hole or groove in the printed circuit board, and controlling the irradiation position of the laser beam at the stored position of coordinates by the scanning device, and a judging unit for judging approval or rejection of the inspection result at each position of coordinates on the basis of the output of the detector.

Therefore, the irradiation position of laser beam by the scanning device depending on the stored position of coordinates is controlled by the controller. The judging unit judges approval or rejection at each position of coordinates on the basis of the output signal of the detector.

Further, this inspection apparatus further comprises a focusing unit for focusing the laser beam emitted from the laser oscillator, and an image transfer optical system and a mask member disposed between the laser oscillator and the focusing unit.

Therefore, the laser beam can be emitted to the printed circuit board in a beam shape of a same shape as the hole shape of the mask member such as perfect circle.

Further, in this inspection apparatus, the beam diameter of the laser beam emitted to the printed circuit board to be inspected is set smaller than the diameter of stop hole or width of the groove.

Therefore, even if there is a slight positioning error, the laser beam will not go out of the stop hole or the groove, and accurate inspection is possible.

Further, in this inspection apparatus, approval or rejection is judged by emitting a spot of laser beam to a plurality of positions of one stop hole or the groove to be inspected.

Therefore, a laser beam spot is emitted to the plurality of positions for one stop hole, so that an accurate inspection is realized.

Further, in this inspection apparatus, approval or rejection is judged by scanning the stop hole or the groove in a cross form.

Therefore, approval or rejection can be judged without scanning the entire stop hole or the groove.

Further, in this inspection apparatus, the detector has optical elements disposed in an array, and is designed to issue signals from each optical element.

Therefore, approval or rejection can be judged by the detector on the image of the reflected light from the printed circuit board to be inspected.

Further, this inspection apparatus further comprises a camera, and a spectroscope disposed on the way of an optical path of reflected light from the printed board for separating the reflected light from the printed circuit board into the detector and camera.

Therefore, approval or rejection can be judged by the camera on the image of the reflected light from the printed circuit board to be inspected.

Further, this inspection apparatus further comprises a light shielding unit for selectively shielding the propagation of the laser beam emitted from the laser oscillator and the reflected light from the printed circuit board.

Therefore, it avoids unexpected emission of laser beam to the printed circuit board, or input of the reflected light from the printed circuit board into the laser oscillator side.

Further, in this inspection apparatus, the criterion is set on the basis of the light intensity of the resin part of the printed circuit board to be inspected actually measured before start of inspection, and the light intensity of normal hole.

Therefore, approval or rejection is judged accurately regardless of the type of the resin part of the printed circuit board or lowering of intensity of laser beam.

Further, in this inspection apparatus, trouble of the laser oscillator or the like is self-diagnosed on the basis of the light intensity of the printed circuit board to be inspected actually measured before start of inspection.

Therefore, trouble of the laser oscillator or the like is self-diagnosed before start of inspection by the light intensity of the printed circuit board to be inspected.

Further, this inspection apparatus further comprises a laser detector for detecting the intensity of the laser beam emitted from the laser oscillator, in which approval or rejection is judged by the output signal of the detector and output signal of the laser detector.

Therefore, approval or rejection can be judged correctly regardless of lowering of intensity of laser beam or the like.

Further, in this inspection apparatus, a test piece is fixed at a specified position, and a laser beam is emitted to the test piece to detect the irradiation position, and thereby the error of the optical system is corrected.

Therefore, the error of the optical system can be corrected automatically.

Further, this inspection apparatus further comprises a temperature detecting unit and a humidity detecting unit, in which the error of the optical system is corrected when the temperature detected by the temperature detecting unit or the humidity detected by the humidity detecting unit is changed more than a specified value.

Therefore, the error of the optical system is corrected automatically when the temperature or humidity is changed more than specified.

Further, in this inspection apparatus, the error of the optical system is corrected periodically at every specified interval.

Therefore, the error of the optical system is corrected automatically upon every lapse of specified time.

Further, this inspection apparatus further comprises a laser oscillator for re-processing, and a laser optical path selector for emitting the laser beam of the laser oscillator for re-processing selectively to the printed circuit board with the same optical axis as the laser beam of the laser oscillator for inspection, in which the defective part is corrected by emitting the laser beam of the laser oscillator for reprocessing to the processing part of the stop hole or the like judged to be defective.

Therefore, the defective part can be corrected accurately on the inspection apparatus.

Further, in this inspection apparatus, the position of coordinates at the location of a defective part is stored, and the defective part is processed after inspection of one printed circuit board.

Therefore, the defective part can be corrected accurately and efficiently on the inspection apparatus.

Further, this inspection apparatus further comprises a collimation mechanism for changing the beam diameter of the laser beam emitted from the laser oscillator, in which the defective part is corrected by emitting a laser beam of a beam diameter reduced from that of inspection by the collimation mechanism, to the processing part of the stop hole or the like judged to be defective.

Therefore, the defective part can be corrected accurately on the inspection apparatus without requiring the laser oscillator for re-processing.

Further, in this inspection apparatus, the defective part is processed, starting from a carbide area near the defective part.

Therefore, the defective part can be corrected accurately on the inspection apparatus without reducing the beam radius so precisely.

Further, in this inspection apparatus, a processing substrate for correction is processed, and the error of the optical system is corrected by detecting this processing position.

Therefore, by processing the processing board for correction, the error of the optical system can be corrected by detecting this processing position.

Further, in this inspection apparatus, an annular or cross shape is processed, and the error of the optical system is corrected by detecting this processing position.

Therefore, if the aperture of the processed hole is small, the error of the optical system can be corrected by detecting this processing position.

BEST MODE FOR CARRYING OUT THE INVENTION

Figure 1:
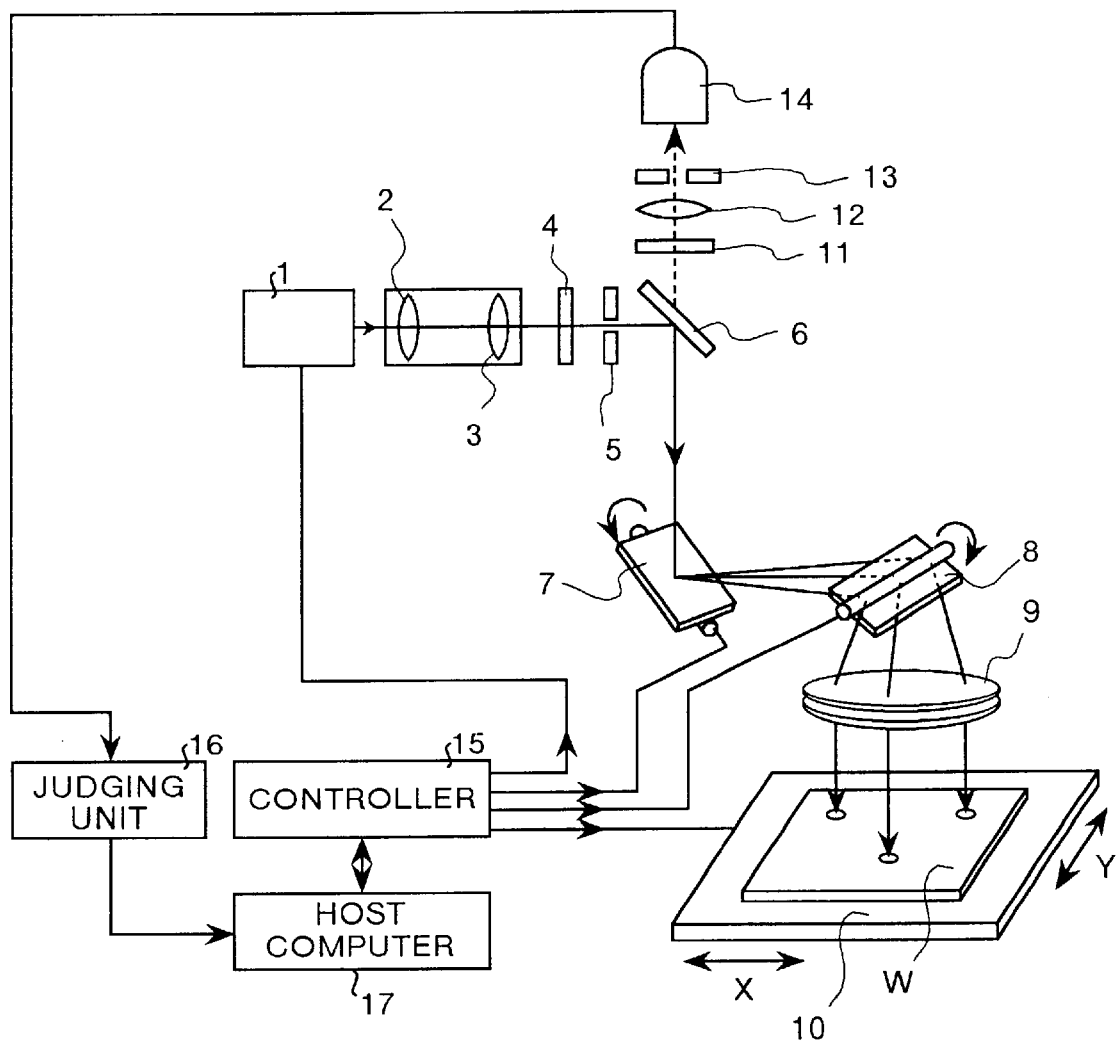
FIG. 1 is a structural diagram showing a first embodiment of an apparatus for inspecting a printed circuit board of the invention.

The invention will be more specifically described below while referring to the accompanying drawings. The inspection apparatus comprises a laser oscillator 1, a collimator lens 2 for adjusting the beam diameter of laser beam emitted from the laser oscillator 1, an image transfer optical system 3, a fluorescence shielding filter 4, a mask plate 5, a dichroic mirror 6 for reflecting the laser beam emitted from the laser oscillator 1 and passing fluorescence, a first galvanomirror 7 for scanning the laser beam in the Y-axis direction, a second galvanomirror 8 for scanning the laser beam in the X-axis direction, a scan lens 9 composed of fθ lens or the like for focusing the laser beam scanned in the Y-axis direction and X-axis direction by the first galvanomirror 7 and second galvanomirror 8 on the printed circuit board W to be inspected, an XY table device (XY stage) 10 on which the printed circuit board W to be inspected is mounted, a filter 11 for selecting the wavelength of the fluorescence passing through the dichroic mirror 6 from the printed circuit board W irradiated with laser beam, a re-focusing lens 12 for re-focusing the fluorescence, a pin hole member 13 for cutting off unnecessary information on the focal plane after passing of the re-focusing lens 12, a fluorescence detector 14 for detecting the fluorescence passing through the pin hole member 13, a controller 15, and a judging unit 16.

The first galvanomirror 7 and second galvanomirror 8 have mutually orthogonal rotary shafts. By the combined movement of the first and second galvanomirrors 7, 8 and the scan lens 9, the irradiation position of laser beam can be set at any position in the mutually orthogonal X-axis direction and Y-axis direction.

The controller 16 controls the operation of the laser oscillator 1, first galvanomirror 7, second galvanomirror 8, and XY table device 10 by the command from a host computer 17 installed in the central processing room.

The judging unit 16 receives a fluorescence intensity signal from the fluorescence detector 14, and judges approval or rejection by discriminating whether the fluorescence intensity is blow the approval judging value or not, and transmits the result of judgement to the host computer 17.

Figure 2:
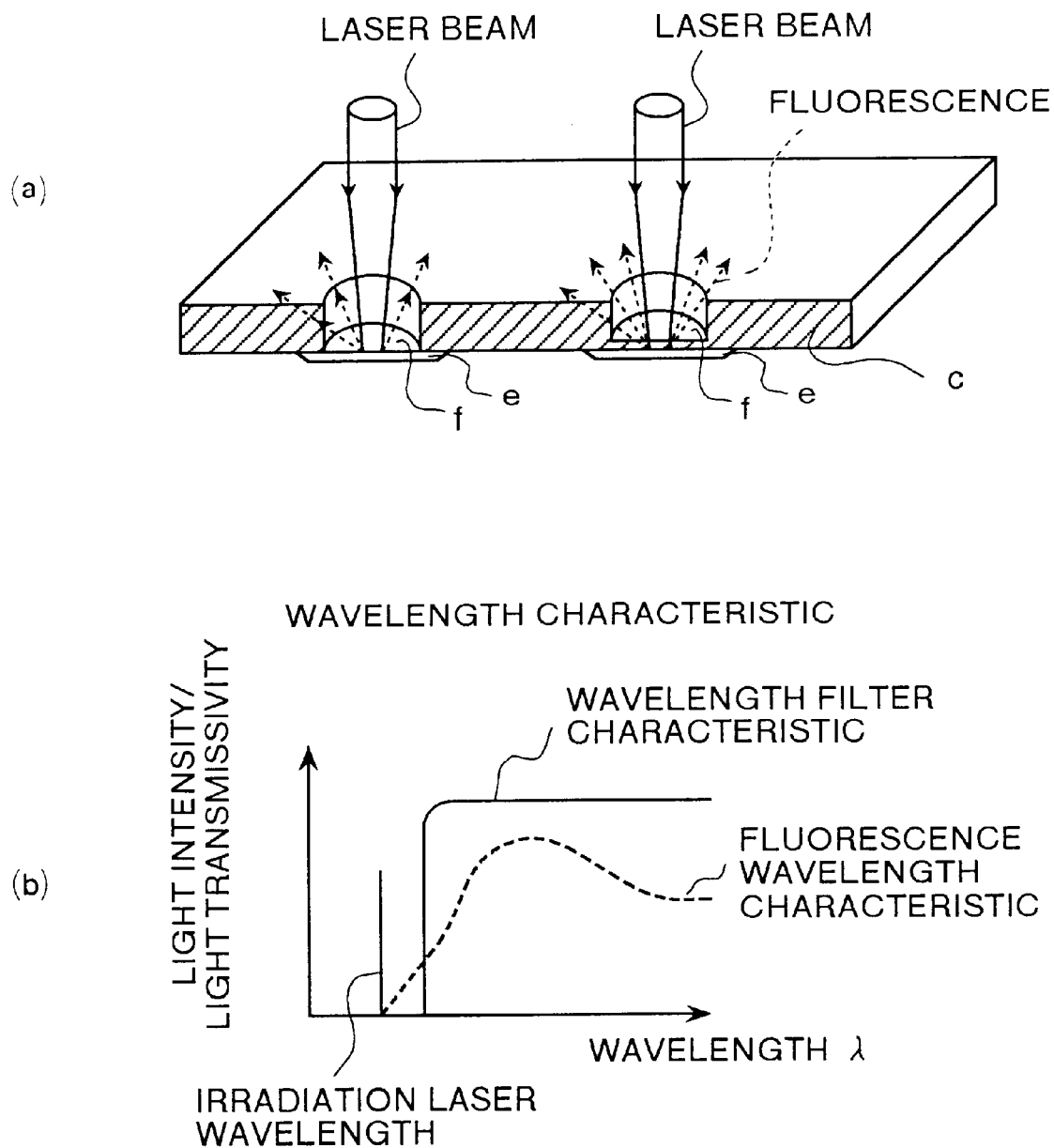
FIG. 2(a) is an explanatory diagram schematically showing a mode of generation of reflected light by fluorescence when the resin residual part is irradiated with laser beam.
FIG. 2(b) is a graph showing the relation between wavelength of laser beam and wavelength of fluorescence.

This inspection apparatus makes use of the phenomenon that fluorescence is generated when laser beam is emitted to the resin or residual resin of stop hole or groove processing part as shown in FIG. 2(a). The fluorescence emits, as shown in FIG. 2(b), light of longer waveform (generally visible light) than the waveform of laser beam. The dichroic mirror 6 is designed to reflect the laser beam emitted by the laser oscillator 1, but pass rays of other wavelength. The filter 11 is used for selecting the light entering the fluorescence detector 14 only at the wavelength to be inspected.

Hitherto, for observation of fluorescence, since the ultraviolet ray is higher in fluorescence intensity at the same laser power, the ultraviolet ray has been generally used. However, the ultraviolet ray is larger in absorption and loss unless a special optical system such as quartz glass is used, and the optical system becomes expensive. Hence, it was decided after experiment that the laser oscillator 1 of 2ω solid laser of wavelength 473 nm, 30 mW should preferably used.

The filter 4 at the laser oscillator 1 side passes light of wavelength of 450 to 490 nm, and the dichroic mirror 6 is designed to reflect light of 495 nm or less. The filter 11 at the fluorescence detector side does not pass light of 520 nm or less. Carbon dioxide laser is used for processing stop holes on the printed circuit board.

By varying the number of shots of carbon dioxide laser, the fluorescence intensity is compared in Table 1 between the mercury lamp and laser beam (in the table, the exposure time (second) is shown, and the light intensity is the reciprocal number of the indicated value) before desmearing process.

TABLE 1

| No. of pulses | Mercury light | lamp 30 mW laser light | Before desmearing |
| --- | --- | --- | --- |
| 3 pulses | 280 | 10 | Defective |
| 5 pulses | 300 | 14 | Defective |
| 7 pulses | 370 | 104 | Conforming |

In this printed circuit board, after pulse processing with 7 shots, it was desmeared, and residual resin was not observed. It has been confirmed that the residual resin can be removed by later desmearing process as far as the residual resin in the stop hole bottom of the printed circuit board is about 0.2 to 0.6 μm.

According to Table 1, in the case of mercury lamp light, the light intensity is similar in both defective and conforming pieces, but in the case of laser beam, the fluorescence intensity differs about 10 times between defective and conforming pieces.

As explained in the prior art, if processing is normally finished, a residual resin of less than 1 μm is left over in the bottom of the stop hole. The laser beam matched in phase with monochromatic nature is absorbed and fluorescence is generated even in the case of a very thin resin of about wavelength, but in the case of mercury lamp light not matched in phase, the light passes through the thin resin and fluorescence is not generated, and inspection is disabled, and the intensity of the fluorescence itself is too low on the whole, and it is found difficult to judge.

The residual resin of about 0.6 μm in the bottom of hole can be removed by desmearing process, and it is not defective, but if the residual resin is thicker, it cannot be removed by desmearing process, and hence it is known effective to detect defective processing before desmearing process after processing with carbon dioxide laser.

In our experiment, the laser beam of wavelength of 473 nm is used, and the residual resin of 0.5 μm or more will be substantially detected sufficiently.

The pin hole member 13 is, different from the prior art, disposed on the focal plane instead of the image transfer plane. Accordingly, the fluorescence intensity is not lowered, and other light than the intended fluorescence can be cut off, and hence inspection of high S/N ratio and high sensitivity is possible.

In Japanese Patent Application Laid-Open No. 7-83841, the object of inspection is scanned by laser beam by using a rotating polyhedral mirror, but the entire printed circuit board must be scanned, and it takes too much time. Or in the combination of the rotating polyhedral mirror and scan lens alone, the scan lens is ø200 mm at maximum, and only a region of about 120 mm×120 mm can be covered.

To cover a wider region, the distance between the scan lens and printed circuit board must be increased 10 to 100 times, and the required focal length of the scan lens is 10 to 100 times, and the spot size on the printed circuit board is too wide, and it is difficult to detect fluorescence. To detect this spot size, the required power of laser beam is 100 to 10,000 times, and it is hard to cover the size of the generated printed circuit board of 600 mm×500 mm.

In the inspection apparatus of the invention, since the scanning optical system is composed by using first and second galvanomirrors 7, 8, by registering the position of coordinates on the printed circuit board W of the stop hole or groove processing part preliminarily in the host computer 17, the irradiation position of laser beam can be set at the stop hole or the groove from the beginning so as to be inspected, without requiring raster scan or other technique. Hence, high speed inspection is enabled.

Figure 3:
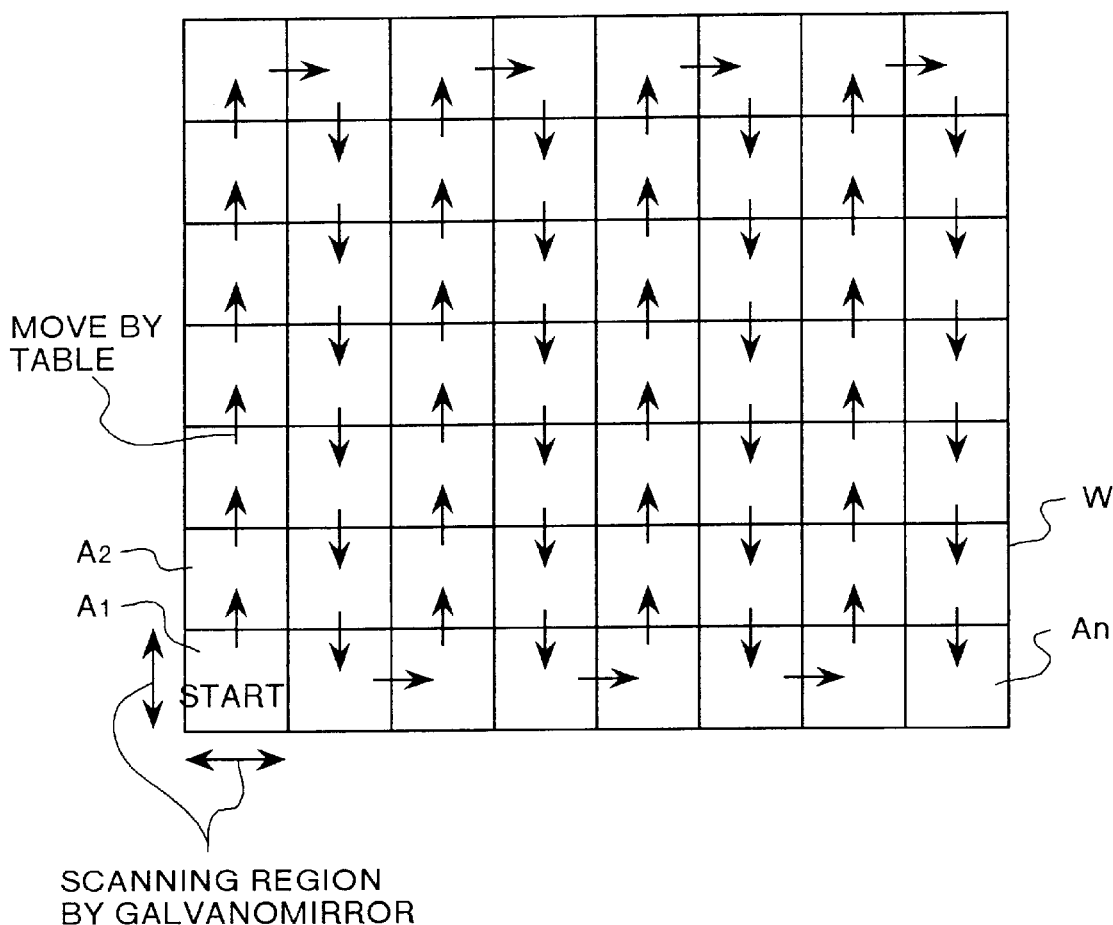
FIG. 3 is an explanatory diagram showing division of scanning region by galvanomirror.

The limit of scanning region is of a same level as when using the rotating polyhedral mirror, but when the printed circuit board W is divided, for example as shown in FIG. 3, into galvanomirror scanning regions A1, A2, . . . , An of about 50 mm×50 mm, and the printed circuit board W is moved, after finishing one region, to next region by XY move of the XY table device 10, thereby starting inspection of next region, the entire region of the printed circuit board can be scanned.

Of course, for faster operation, the XY table device 10 and galvanomirrors 7, 8 may be moved simultaneously.

In this embodiment, the galvanomirrors (galvanoscanners) are used, but same effects are obtained by scanning by using AO (acousto-optical elements) or EO (electromagnetic-optical elements).

In the inspection apparatus shown in FIG. 1, the collimator lens 2 is disposed after the laser oscillator 1, and the image transfer optical system 3 and the mask plate 5 having a central pass hole are disposed behind them.

The reason why the image transfer optical system 3 and mask plate 5 are disposed like this is explained below. For example, when the laser oscillator 1 is a semiconductor laser or slab type laser, the intensity distribution of laser beam is not always uniform in vertical and lateral direction, or the divergence angle may be different or the M2 value (focusing performance) may be different in vertical and lateral direction. In such a case, when the laser beam is directly propagated and focused by the scan lens 9, an elliptical profile may be formed at the focal position while the characteristic of the laser beam is unchanged. The image transfer optical system 3 and mask 4 are used in such a case.

The laser beam is adjusted by the image transfer optical system 3 so as to be slightly larger than the hole diameter of the mask plate 5. The foot of the laser beam is cut off by the mask plate 5. That is, at the mask exit, the laser beam in the shape of the hole of the mask is obtained. Supposing the distance from the mask to the scan lens to be La, the distance between the scan lens and printed circuit board to be Lb, and the focal length of the scan lens 8 to be f, a beam of a similar shape as the mask hole shape is obtained a gain at the position of $$(1/La)+(1/Lb)=1/f.$$

For example, when the hole shape of the mask plate 5 is a perfect circle, a laser beam of true circle is emitted to the printed circuit board.

Figure 4:
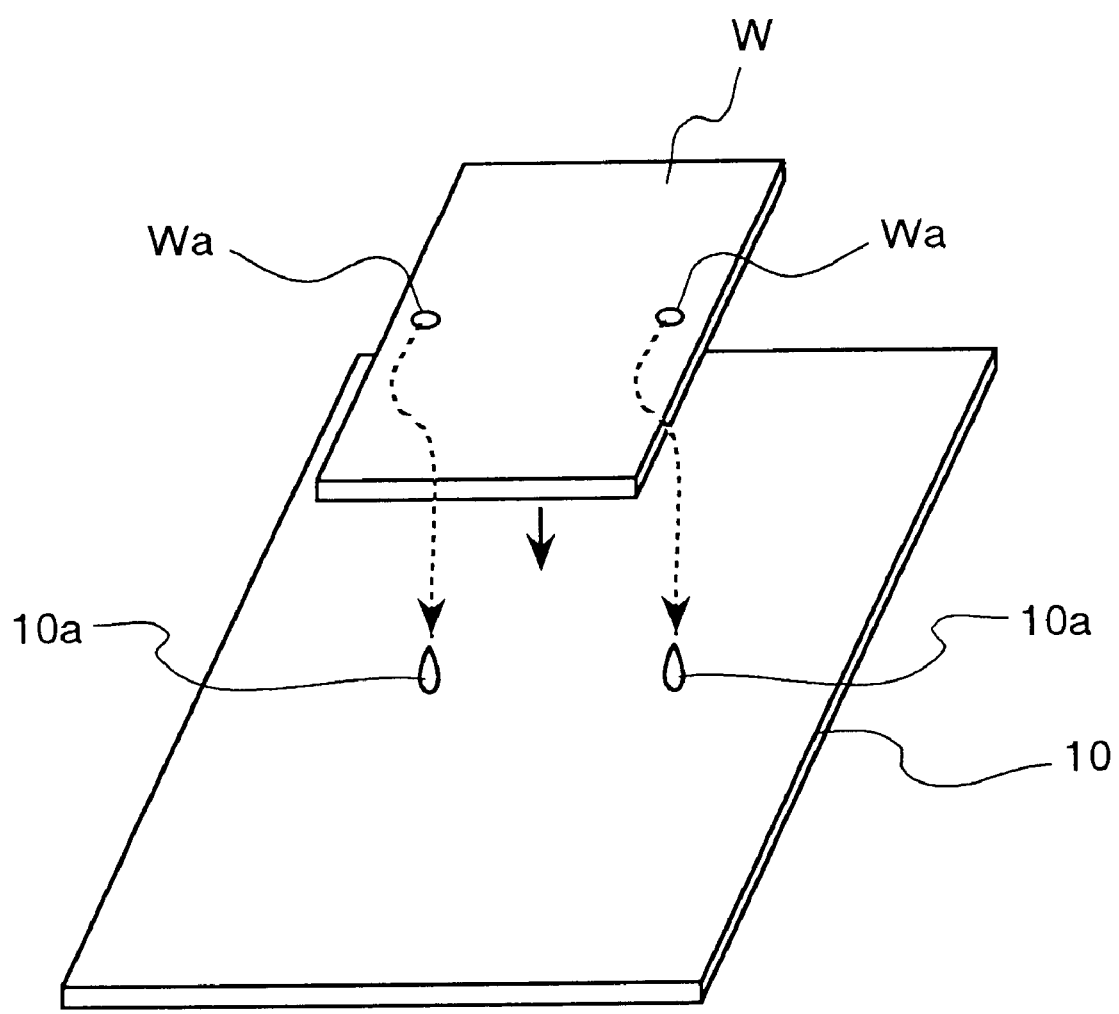
FIG. 4 is a perspective view showing a positioning structure of printed circuit board to be inspected.

Generally, as a mechanism for detecting the same coordinates between different devices, as shown in FIG. 4, two or more positioning holes Wa are provided in the printed circuit board W, and positioning pins 10a are inserted into the positioning holes Wa from the table side, so that position is determined. This positioning causes a positioning error of only about 10 $\mu$m. Besides, the positioning error of scanning system of galvanomirrors or the like is about 10 to 20 $\mu$m, and the table positioning error is about 5 $\mu$m, and hence, on the whole, a positioning error of about 30 $\mu$m is inevitable.

Figure 5:
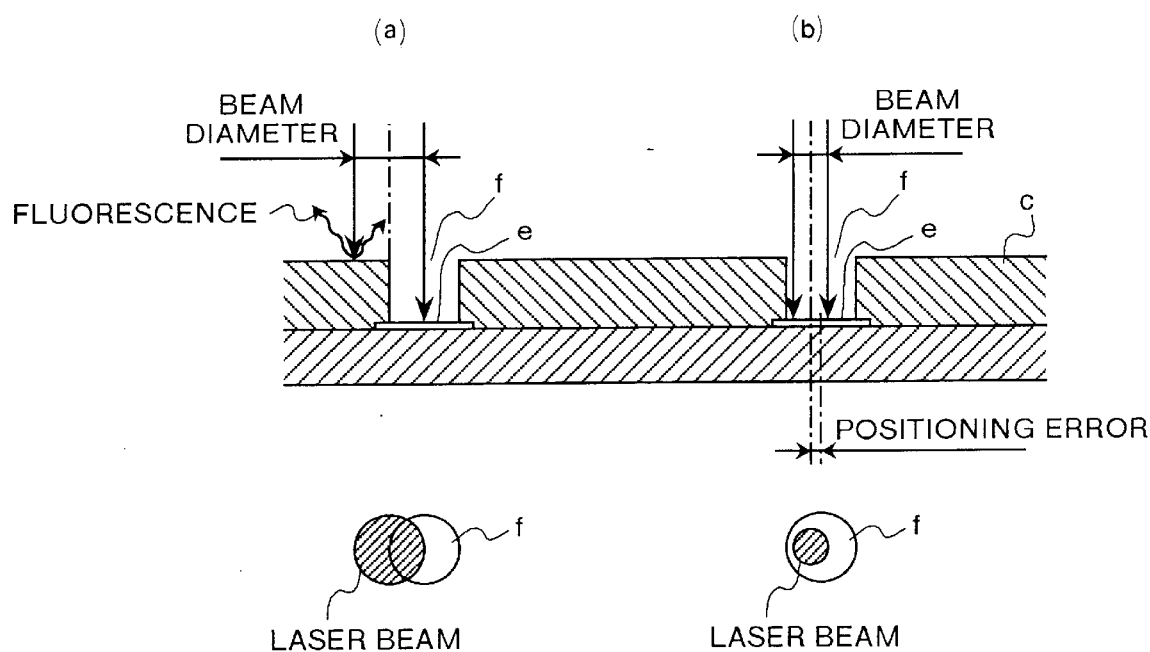
FIGS. 5(a) and (b) are explanatory diagrams showing the configuration of stop hole and laser beam.

When the beam diameter of the laser beam emitted to the printed circuit board W is larger than the diameter of the stop hole f, there is a case of inspection by emitting the laser beam to the position as shown in FIG. 5(a). In this case, if the stop hole is normal, the fluorescence from the resin around the hole enters the fluorescence detector 14, and it is hard to judge approval or rejection.

However, when detecting the hole with an aperture of, for example, 100 $\mu$m by the inspection apparatus having the precision as mentioned above, by irradiating the printed circuit board W with laser beam of beam diameter of 100 $\mu$m−30 $\mu$m=70 $\mu$m or less, as shown in FIG. 5(b), the laser beam is not outside of the stop hole f, and conforming or defective piece can be judged stably. Hence, the inspection apparatus of high reliability is obtained. In the case of groove processing, the beam diameter may be set smaller than the groove width.

Reduction of beam diameter brings about further benefits, that is, the light density per unit increases, the fluorescence intensity is higher, the S/N ratio is raised, and the reliability is higher.

Figure 6:
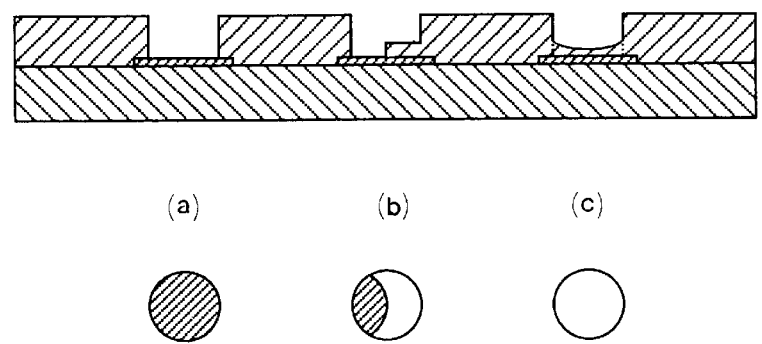
FIGS. 6(a) to (c) are explanatory diagrams schematically showing modes of remaining of resin in the stop hole.

Modes of residual resin in the stop hole include the cases as shown in FIGS. 6(a) to (c). FIG. 6(a) shows a normal piece, and even in a normal piece, there is a residual resin of about 1 $\mu$m on the copper foil. In FIG. 6(b), part of the stop hole is normal, but the residual resin is thick in some portion, and it is difficult to remove by desmearing. FIG. 6(c) shows a defective piece, that is, the residual resin is thick on the whole, and it cannot be removed by desmearing.

In the case of the stop hole shown in FIG. 6(b), it is conducted when plated, and may be regarded to be conforming, but in the case of inspection by laser beam irradiation of one position, only the residual resin may be inspected, possibly resulting in rejection.

Figure 7:
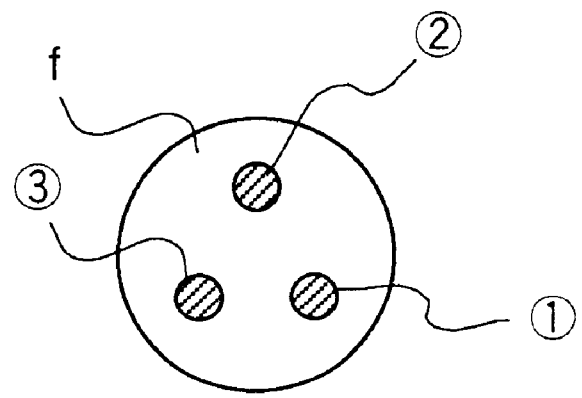
FIG. 7 is an explanatory diagram schematically showing the mode of emission of spot laser beam to the plurality of positions of one stop hole.

Accordingly, instead of inspecting one stop hole by emitting laser beam to one position only, as shown in FIG. 7, the beam diameter is reduced, and one stop hole f is inspected by emitting laser beam spot to the plurality of positions 1 to 3.

Figure 8:
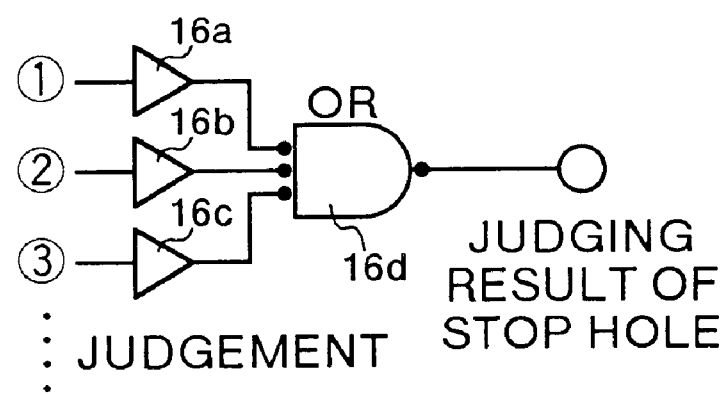
FIG. 8 is a logic circuit diagram showing a signal processing circuit in the case of emission of spot laser beam to the plurality of positions of one stop hole.

In the case of inspection by laser beam irradiation at one position, only the residual resin in FIG. 6(b) is inspected, and it may result in rejection, but when one stop hole f is inspected by emitting laser beam spot to the plurality of positions 1 to 3, as shown in FIG. 8, the fluorescence intensity at each irradiation position is judged by judging units 16a to 16c, and results of judgement are put into an OR gate 16d, and if approval is judged at any one of the plurality of positions in the outputs of the OR gate 16d, the corresponding stop hole may be judged to be conforming.

Besides, if necessary to judge rejection when the residual resin occupies ⅓ of the hole, it may be designed to be judged affirmatively if it is normal in ⅔ of several positions of the stop hole irradiated with laser beam. By such processing, the yield is improved, and the inspection of high reliability is realized.

Such configuration is particularly effective when processing the printed circuit board directly, but in the case of conformal processing or the like, positioning of substrate may be largely deviated, or the precision of the galvanomirrors 7, 8 may be poor, and the irradiation position and stop hole position may be largely deviated.

In the case of conformal processing, since there is a copper substrate on the irradiation plane, and fluorescence is not emitted, and it may be mistaken to be normal. In such a case, it is also necessary to emit by isolating the plurality of irradiation positions by a sufficiently long distance as compared with the hole diameter.

Whether in the substrate by conformal processing or in the substrate by direct processing, in order to inspect in the minimum time, preferably, it should be set so as to inspect one stop hole by irradiation at one position or by irradiation at the plurality of positions, and also to change the setting of the distance of the plurality of positions depending on the hole diameter and processing method.

Figure 9:
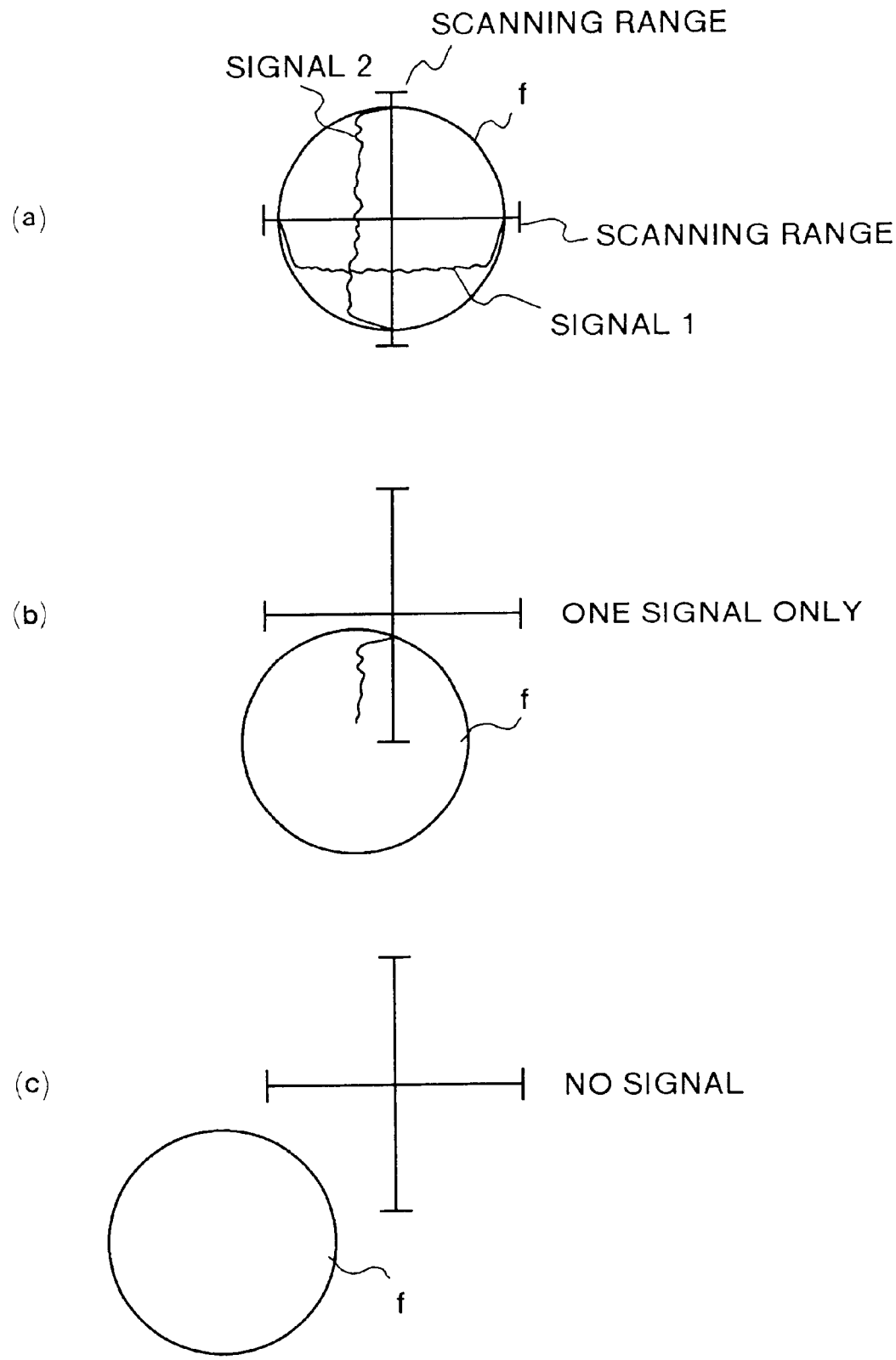
FIGS. 9(a) to (c) are explanatory diagrams showing the relation of positional error of signal output and stop hole in the case of cross scanning.

Further, on the basis of the position information of the hole processing part to be inspected, as shown in FIG. 9(a), by scanning in a cross form by the distance corresponding to the hole diameter of the stop hole f, approval or rejection may be judged by signal 1 and signal 2 of the fluorescence signal obtained by this scanning.

In this inspection, all holes are not scanned, and it is possible to scan at high speed, and as shown in FIG. 9(b), when the processing position of the stop hole f is deviated, the amount of deviation can be measured from signal 1 and signal 2.

Or, as shown in FIG. 9(c), if the stop hole f is not checked by the cross, it is judged to be defective, and if the deviation amount is more than the allowable value, it is also judged to be defective. Moreover, by the fluorescence distribution by cross scanning, the residual resin or hole shape (degree of taper, etc.) can be measured, so that approval or rejection of the hole processing part or groove processing part may be judged more specifically.

The output of the laser oscillator 1 may fluctuate due to some cause (environmental temperature, device temperature, life of optical system, soiling), and the intensity of fluorescence may vary accordingly. When the laser output drops largely, the fluorescence also drops largely, and it may be possibly misjudged to be normal. Moreover, since the intensity of fluorescence varies significantly depending on the composition of the resin, it is necessary to inspect before starting inspection. Further, depending on the printed circuit board manufacturing line, the resin of the printed circuit board may be FR-4, epoxy, polyimide, etc., and various substrates flow in the manufacturing line, and it is necessary to understand the fluorescence intensity of each substrate.

To cope with these matters, by forming a conforming piece hole preliminarily at a place not necessary as product on the printed circuit board, the light intensity of fluorescence in the resin part and the light intensity of the conforming piece hole are inspected before starting inspection of the printed circuit board, and these light intensities are stored in the judging unit 16, and the conforming piece judging value (threshold) can be properly set from these two light intensities.

Figure 10:
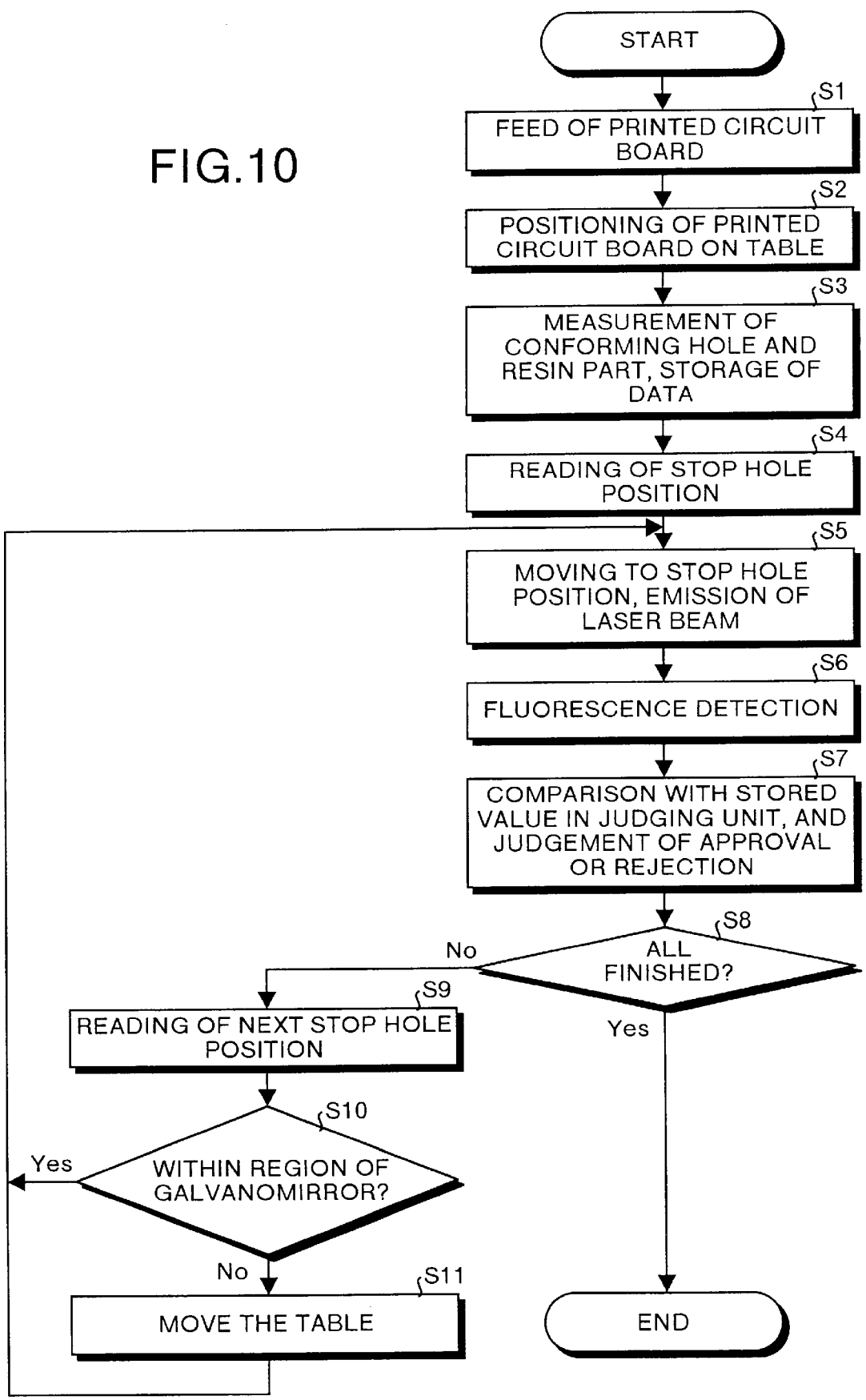
FIG. 10 is a flowchart showing an inspection process procedure of printed circuit board.

Referring now to the flowchart shown in FIG. 10, the inspection process procedure of printed circuit board by the inspection apparatus of the invention is explained.

First, by a printed circuit board loading device such as a robot, the printed circuit board W to be inspected is carried onto the XY table device 10 (step S1), and is positioned and set by a pin system or vision sensor (step S2).

Then, measuring the light intensity of the fluorescence at the conforming piece hole preliminarily formed at a place not necessary as product on the printed circuit board W, and the light intensity of the fluorescence of the resin part, these light intensities are stored in the judging unit 16, and the conforming piece judging value is automatically set from these two light intensities by the judging unit 16 (step S3).

Next, reading out the stop hole position to be inspected first on the printed circuit board W being positioned and set, the first and second galvanomirrors 7, 8 are moved by the galvanomirror command, and the laser beam is emitted to the stop hole position (step S5), and the fluorescence is detected by the fluorescence detector 14 (step S6).

This fluorescence detected value and the conforming piece judging value (stored value) set in the judging unit 16 are compared in the judging unit 16, and the approval or rejection is judged (step S7).

After completion of judgement of approval or rejection, it is checked whether inspection is completed about all stop holes to be inspected or not (step S8), and if not completed, the position of the stop hole to be inspected next is read out (step S9), and it is judged whether this position exists in the present scanning region of the galvanomirror or not (step S10). If within the region, directly going back to step S5, the first and second galvanomirrors 7, 8 are moved by the galvanomirror command, and the laser beam is emitted to the stop hole position (step S5), and the fluorescence is detected by the fluorescence detector 14 (step S6).

By contrast, if out of the region, the XY table device 10 is moved until the stop hole position to be inspected next comes into the scanning region of the galvanomirror (step S11), and going back to step S5, the first and second galvanomirrors 7, 8 are moved by galvanomirror command, and the laser beam is emitted to the stop hole position (step S5), and fluorescence is detected by the fluorescence detector 14 (step S6).

In the measurement of light intensity before inspection, depending on the signal of light intensity, it is possible to judge drop of laser output, trouble of laser oscillator 1, or drop of detection sensitivity or trouble of the detector 14, and when constituted to display a message or stop the device in such a case, a highly reliable inspection apparatus having a self-diagnostic function is obtained.

Figure 11:
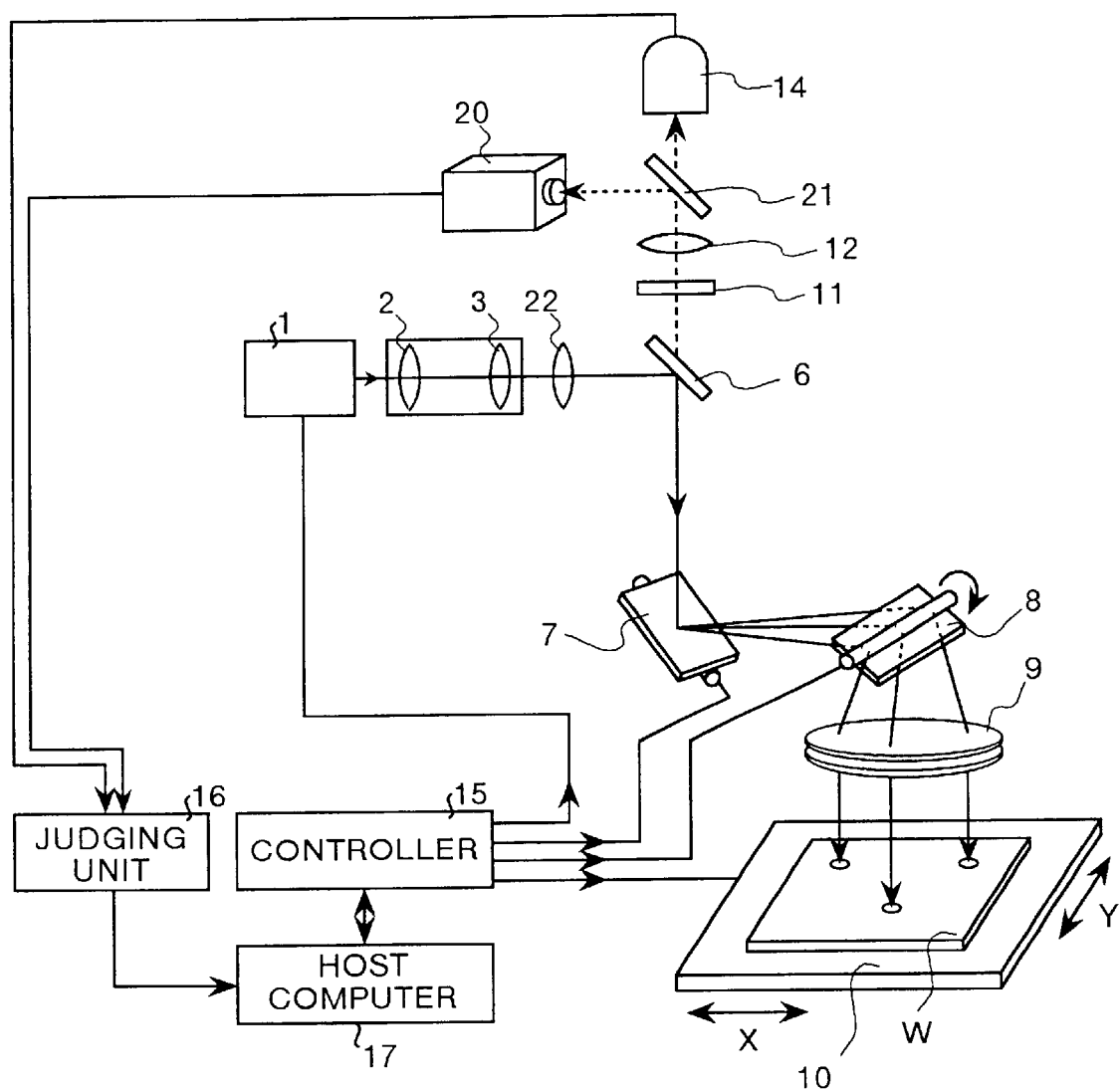
FIG. 11 is a structural diagram showing a second embodiment of an apparatus for inspecting a printed circuit board of the invention.

FIG. 11 shows the second embodiment of an apparatus for inspecting a printed circuit board of the invention. In FIG. 11, same or similar components as shown in FIG. 1 are identified with same reference numerals as shown in FIG. 1, and their explanation is omitted.

This embodiment comprises a camera 20 composed of CCD element and others for detecting an image, a spectroscope 21 for separating the detected light disposed between the refocusing lens 12 and fluorescence detector 14, and a beam diameter adjusting lens 22 for changing the beam diameter of the laser beam issued by the laser oscillator 1 disposed between the image transfer optical system 3 and dichroic mirror 6.

In this embodiment, the laser beam of the same diameter or a larger diameter of the stop hole diameter on the printed circuit board can be emitted to the printed circuit board W by the beam diameter adjusting lens 22.

The fluorescence detector 14 only detects the fluorescence intensity, but the camera 20 can recognize the fluorescence as an image. The spectroscope 21 is composed of, for example, a half-mirror, and it branches the fluorescence from the printed circuit board W into the fluorescence detector 14 and camera 20, so that simultaneous measurement is possible in the fluorescence detector 14 and camera 20.

That is, measurement at the same position is done same as in the first embodiment, and by emitting the laser beam to the entire hole, it can be also measured as an image by the camera 20. The image data of the camera 20 is fed into the judging unit 16, and approval or rejection of the hole processing is judged, thereby measuring simultaneously in the fluorescence detector 14 and camera 20. Measuring simultaneously, only when judged to be normal by both, this hole is judged to be normal, so that a system of a very high redundancy is realized.

The half-mirror 21 may be shutter or optical path changeover means so that either the camera 20 or the fluorescence detector 14 may be allowed to measure.

The beam diameter adjusting lens 22 controls to insert into the laser optical path when measuring with the camera, and not to insert when measuring with the fluorescence detector 14, and therefore when measuring with the camera, the beam diameter of the laser beam emitted to the printed circuit board W can be changed, and the precision of judgement is enhanced.

Figure 12:
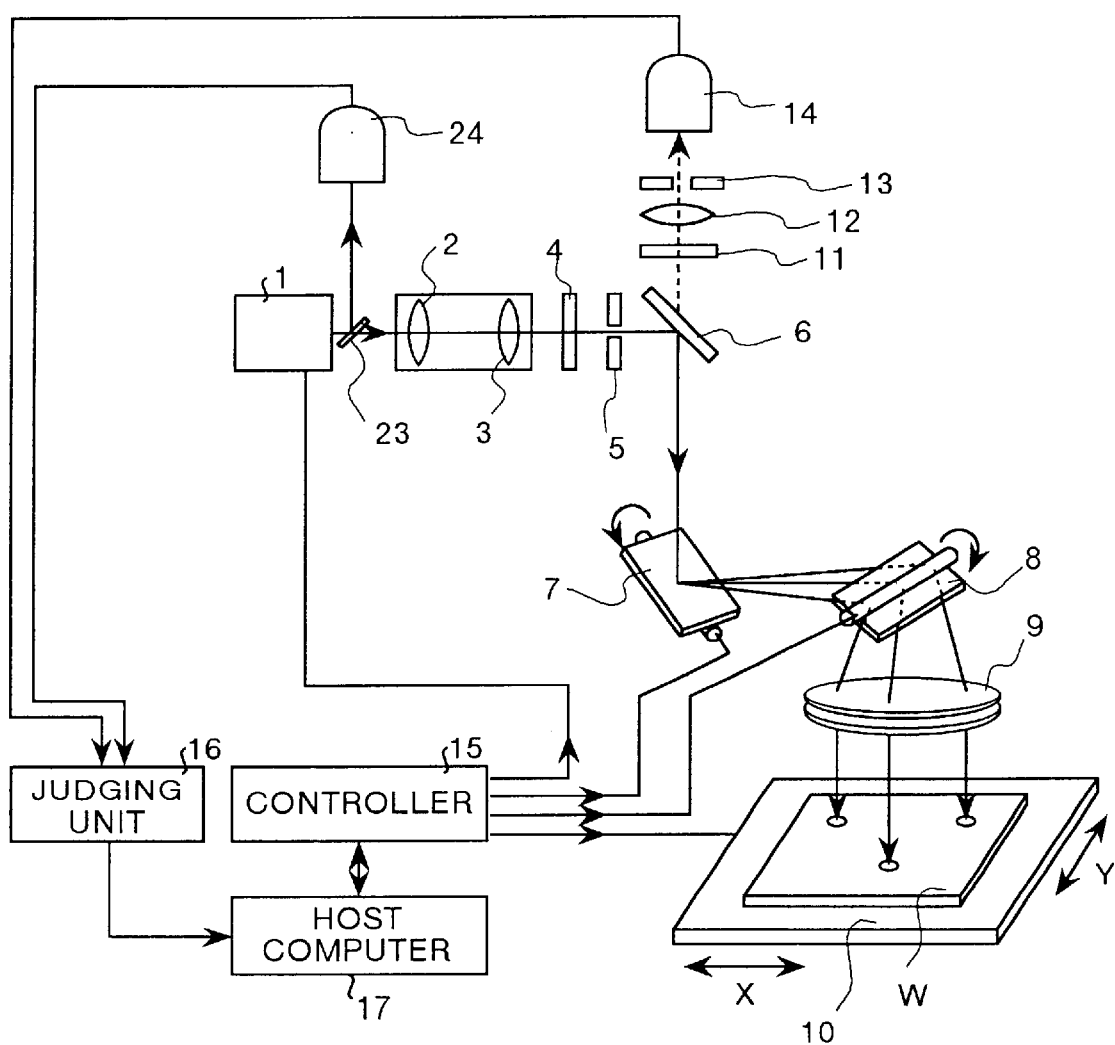
FIG. 12 is a structural diagram showing a third embodiment of an apparatus for inspecting a printed circuit board of the invention.

FIG. 12 shows the third embodiment of an apparatus for inspecting a of printed circuit board of the invention. In FIG. 12, too, same or similar components as shown in FIG. 1 are identified with same reference numerals as shown in FIG. 1, and their explanation is omitted.

This embodiment further comprises, in addition to the first embodiment, a half-mirror 23 for reflecting in part and passing the rest provided in the midst of the laser optical path of the laser oscillator 1, and a laser detector 24 for detecting the intensity of the laser beam reflected by the half-mirror 23.

The reflectivity of the half-mirror 23 is, for example, 10% or less, and the output of the laser beam emitted from the laser oscillator 1 can be spuriously monitored by the laser detector 24.

A laser detection signal $I_0$ issued by the laser detector 24 is sent into the judging unit 16, and a fluorescence intensity signal $I_1$, is sent from the fluorescence detector 14 to the judging unit.

The fluorescence intensity always corresponds to the output emitted to the substrate, and hence the judged value I is expressed as $$I=I_1/I_0.$$

Figure 13:
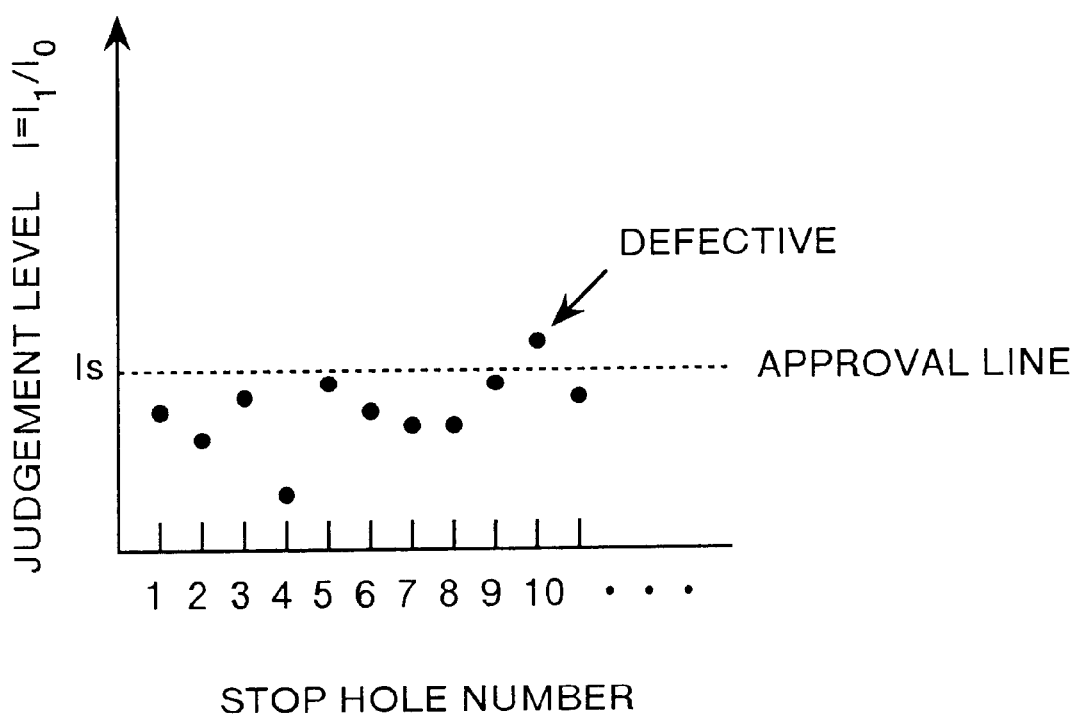
FIG. 13 is a graph showing the relation between the judging level value and judging value.

As shown in FIG. 13, when the judged value I exceeds the judgement level value $I_s$, it is judged to be defective.

Or, when $I_0$ is lowered from the initial value by more than a specified level, it is judged to be a trouble of the laser oscillator 1 by the judging unit 16.

In this configuration, wrong diagnosis of printed circuit board inspection by output change of the laser oscillator 1 is prevented, and the laser oscillator 1 is also diagnosed, so that a reliable inspection is possible.

In the embodiment, the laser detector 24 is disposed near the laser oscillator 1, but same effects are obtained if disposed at any position of the laser optical path from the laser oscillator 1 to the printed circuit board W.

Figure 14:
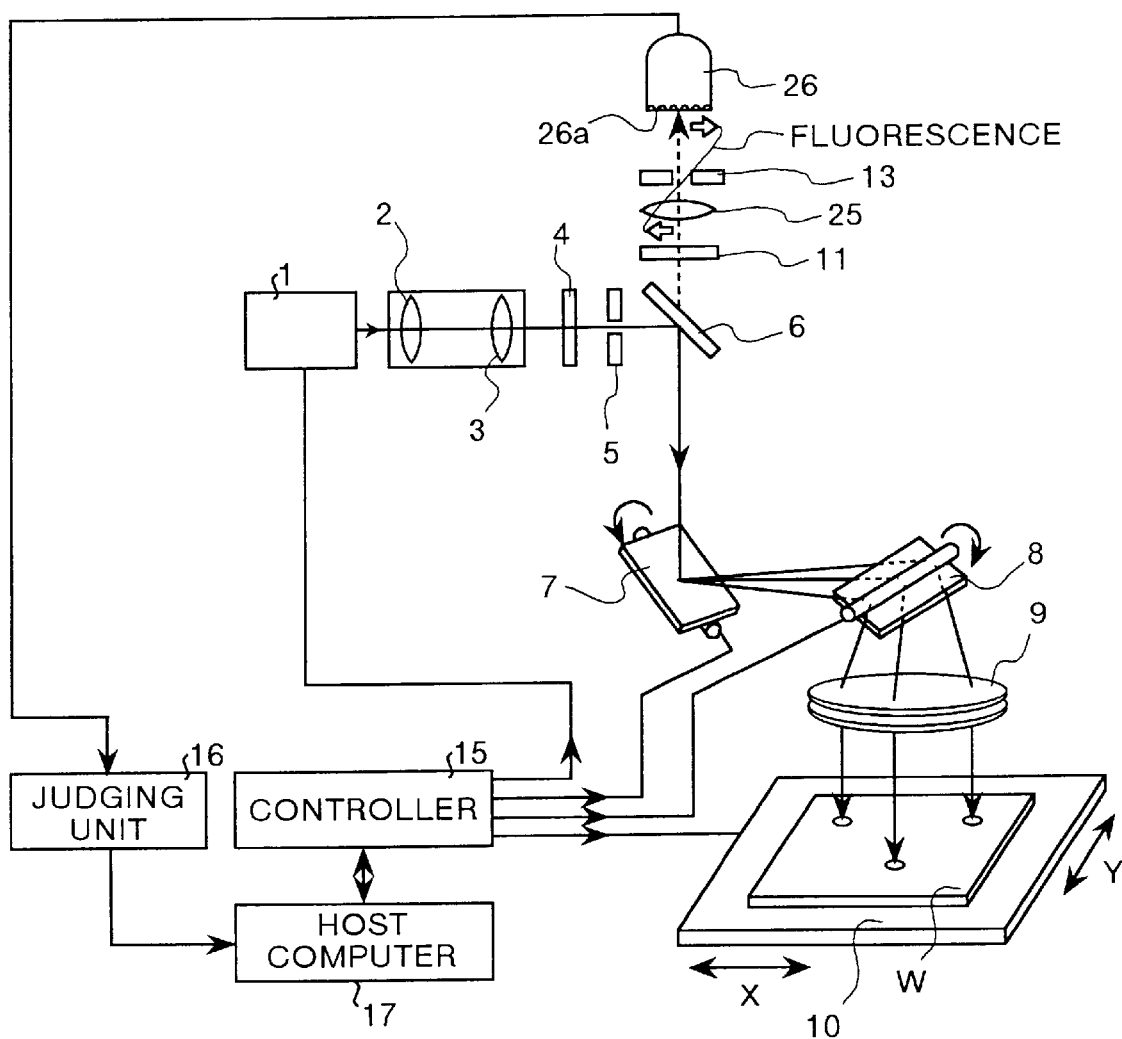
FIG. 14 is a structural diagram showing a fourth embodiment of an apparatus for inspecting a printed circuit board of the invention.

FIG. 14 shows the fourth embodiment of an inspection apparatus for inspecting a printed circuit board of the invention. In FIG. 14, too, same or similar components as shown in FIG. 1 are identified with same reference numerals as shown in FIG. 1, and their explanation is omitted.

In this embodiment, instead of the re-focusing lens 12, an image transfer lens 25 is provided, and the fluorescence detector is an image sensor type fluorescence detector 26 having CCD and other photo diodes disposed on an array. An image of the printed circuit board W is transferred on the fluorescence detecting plane 26a of the fluorescence detector 26 by the image transfer lens 25.

Figure 15:
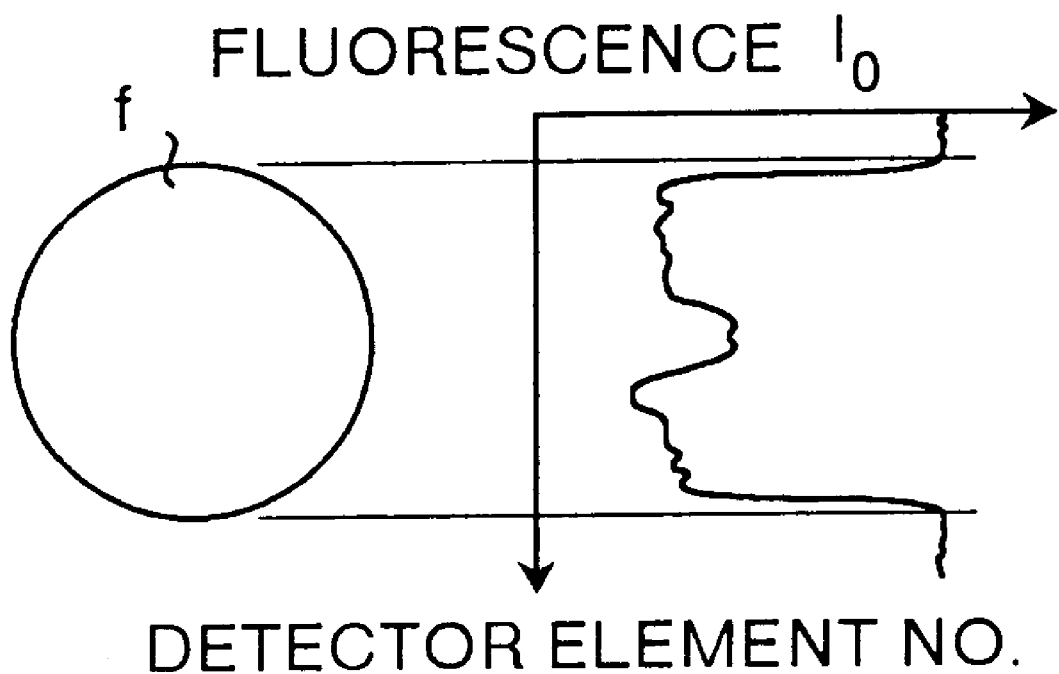
FIG. 15 is a graph showing signal output characteristic of detector of image sensor type.

The laser beam is adjusted by the collimator lens 2 so that the diameter may be, for example, same as the stop hole, and a linear distribution image of fluorescence intensity is obtained in the fluorescence detector 26, and when signals of array-form detectors are issued simultaneously, for example, signals as shown in FIG. 15 are obtained.

As mentioned in the first embodiment, a positioning error occurs, and the laser beam is not precisely matched with the stop hole position. In the case of the stop hole shown in FIG. 6(b), of the 10×10 array, if it is judged to be conforming in a region of, for example, 2×2 or more, this stop hole is judged to be conforming.

In the laser inspection apparatus having such construction, the yield is improved, and the inspection reliability is heightened.

Figure 16:
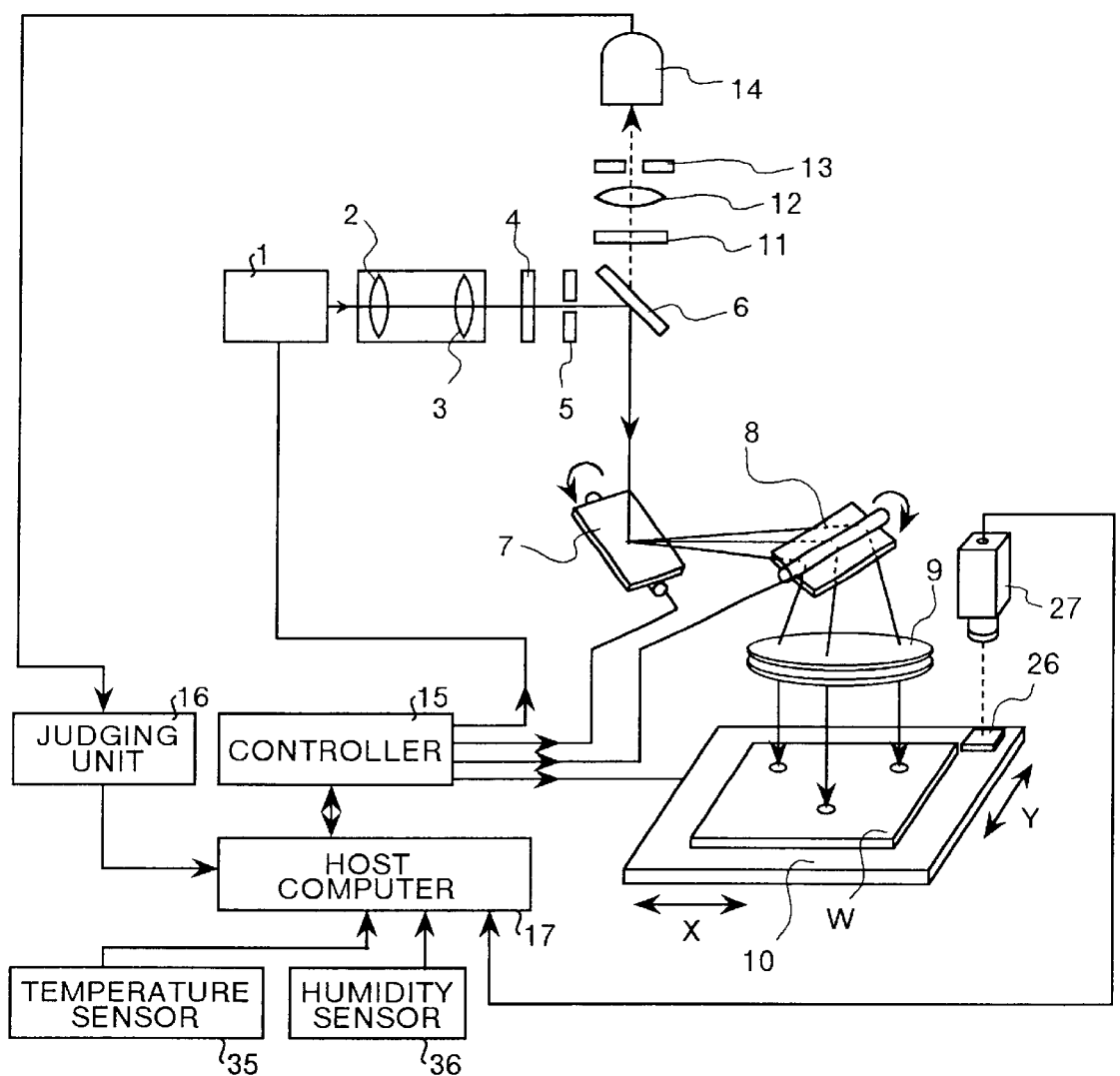
FIG. 16 is a structural diagram showing a fifth embodiment of an apparatus for inspecting a printed circuit board of the invention.

FIG. 16 shows the fifth embodiment of an apparatus for inspecting a printed circuit board of the invention. In FIG. 16, too, same or similar components as shown in FIG. 1 are identified with same reference numerals as shown in FIG. 1, and their explanation is omitted.

In this embodiment, as the correction system for correcting the irradiation position by optical distortion of the scan lens 9, additionally, there are a test piece 56 fixed and disposed at a specified position of the XY table device 10 and a vision sensor 27 for detecting the irradiation position of the test piece 26, and the host computer 17 receives the signal issued by the vision sensor 27.

There are also a temperature sensor 35 for detecting the environmental temperature of the inspection apparatus, and a humidity sensor 36 for detecting the environmental humidity of the inspection apparatus, and the host computer 17 receives the environmental temperature of the inspection apparatus detected by the temperature sensor 35 and the environmental humidity of the inspection apparatus detected by the humidity sensor 36.

Figure 17:
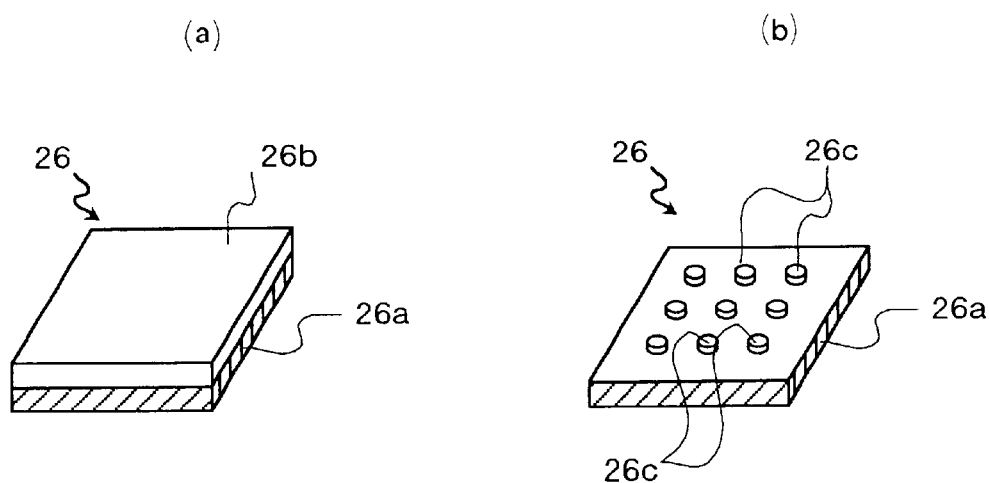
FIGS. 17(a) and (b) are perspective views showing a test piece for position error correction.

The test piece 56 is, for example, a small substrate 26a coated with a paint 26b emitting residual fluorescence as shown in FIG. 17(a), and 3×3 points, for example, are punched on the test piece 56 by the galvanomirrors 7, 8, and the XY table device 10 is moved while the residual fluorescence is being emitted, and the nine points are observed by the vision sensor 27, and the position is corrected.

Figure 18:
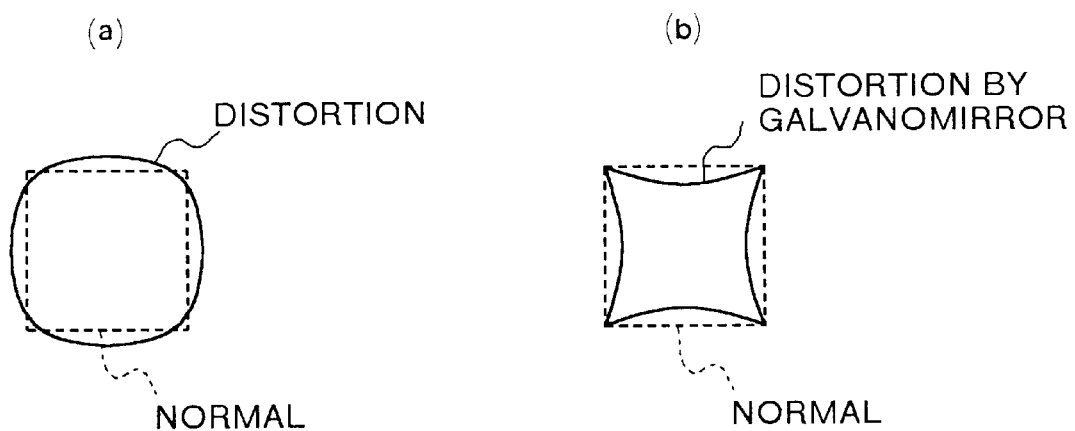
FIGS. 18(a) and (b) are explanatory diagrams showing modes of optical distortion by scanning system.

In the case of scanning of laser beam by the combination of galvanomirrors 7, 8 and scan lens 9, since it is difficult to manufacture the scan lens 9 free from optical distortion, as shown in FIG. 18(a), it is not possible to avoid occurrence of optical distortion such as barrel distortion. It is known that such distortion varies with the environmental temperature and humidity, or deterioration of the scan lens.

The galvanomirrors 7, 8 are scanned in curvature, if the command value is square, in order to issue an angle command as shown in FIG. 18(b).

To correct such distortion, it is necessary to scan the predetermined point before start of inspection and match the position with the position of the mechanical coordinates. Besides, the optical distortion includes environmental and time-course changes, and the positioning, that is, correction of irradiation position must be done periodically.

In this regard, having such correction system, the irradiation position can be corrected whenever desired, and the laser beam can be always emitted to the target position, and the residual resin around the stop hole can be accurately judged, so that a highly reliable inspection is possible.

As for time-course changes of optical distortion due to deterioration of scan lens or the like, by measuring the time by the timer built in the host computer 17, every time a predetermined time passes, the error of the optical system is corrected, that is, correction of irradiation position is done periodically and automatically.

The host computer 17 receives signals of environmental temperature of the inspection apparatus detected by the temperature sensor 35, and environmental humidity of the inspection apparatus detected by the humidity sensor 36, and if the environmental temperature detected by the temperature detector 35 or the environmental humidity detected by the humidity sensor 36 changes more than a specified value, error correction of the optical system, that is, correction of irradiation position can be done automatically.

In a modified embodiment, the fluorescence detector 26 of the second embodiment may be replaced with the vision sensor 27, which may be used for detection.

The test piece 56 may be, as shown in FIG. 17(b), prepared by applying a spot of fluorescent paint 26c at a desired position, and while detecting the fluorescence intensity by the fluorescence detector 26, correction may be executed so that the output signal of the fluorescence detector 26 may be maximum.

Figure 19:
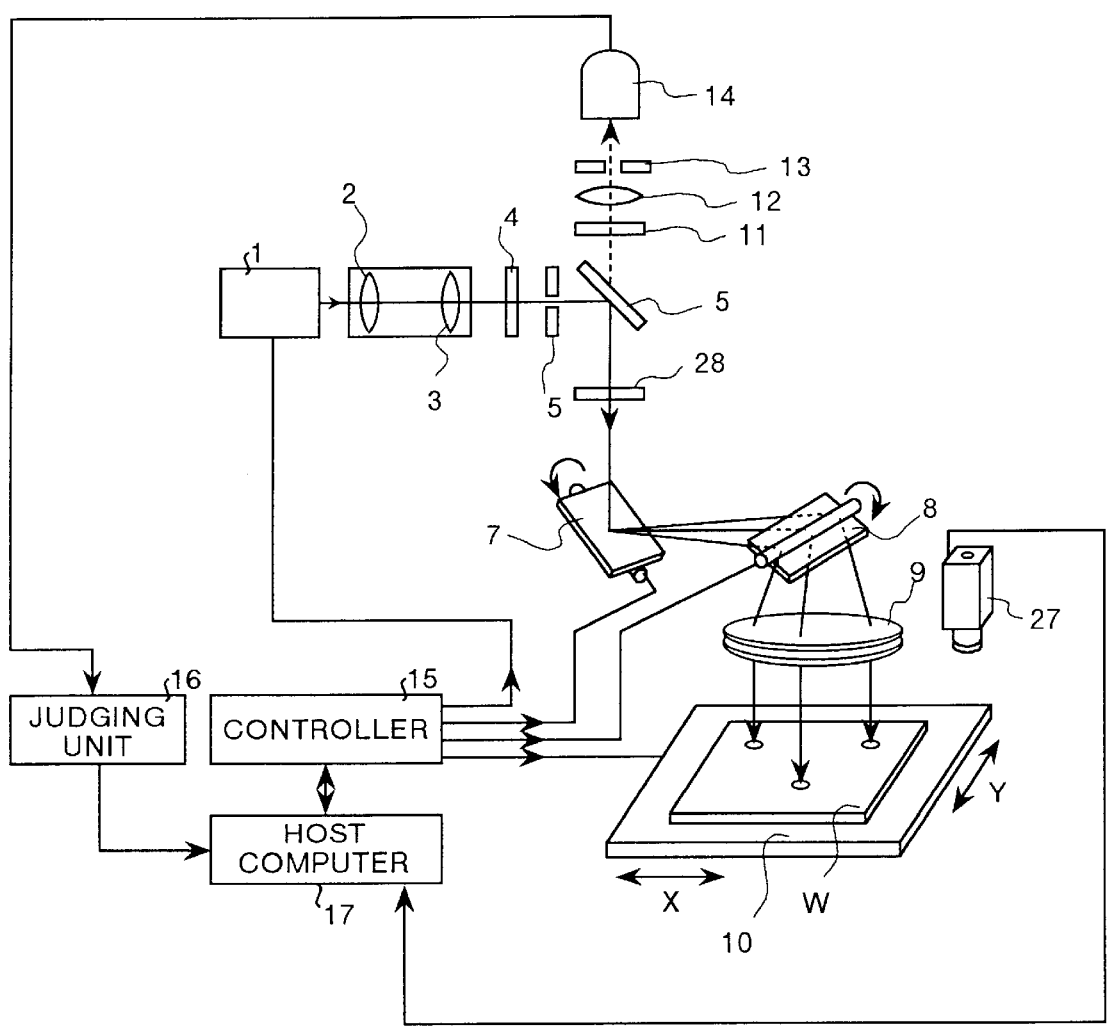
FIG. 19 is a structural diagram showing a sixth embodiment of an apparatus for inspecting a printed circuit board of the invention.

FIG. 19 shows the sixth embodiment of an apparatus for inspecting a printed circuit board of the invention. In FIG. 19, too, same or similar components as shown in FIG. 1 are identified with same reference numerals as shown in FIG. 1, and their explanation is omitted.

In this embodiment, a liquid crystal shutter 28 is provided between the dichroic mirror 6 and first galvanomirror 7 as light shielding means for selectively shielding propagation of laser beam from the laser oscillator 1 and reflected light from the printed circuit board W.

While scanning, since the laser beam is passing above the resin, the laser beam hits against the resin and a strong fluorescence is generated, and it returns to the detecting system and laser oscillator 1, which may damage the fluorescence detector 14 or laser oscillator 1 for a long period.

By installing the filter 4 at the laser oscillator 1 side, it may be protected from the fluorescence. However, the detector cannot be protected. Therefore, while not detecting, the laser beam is not projected to the board.

If a high power laser is used in order to obtain a strong fluorescence intensity difference, the resin may be processed by some factor. If other part than the stop hole or groove processing part is processed, the printed circuit board may be short-circuited or damaged. In this case, too, the laser beam is not projected to the printed circuit board in the non-detecting area other than the stop hole part.

The laser beam may be cut off by a signal from the controller 15 for cutting off supply of current to the light emitting diode or lamp for laser excitation, or may be shielded optically by the liquid crystal shutter 28.

Figure 20:
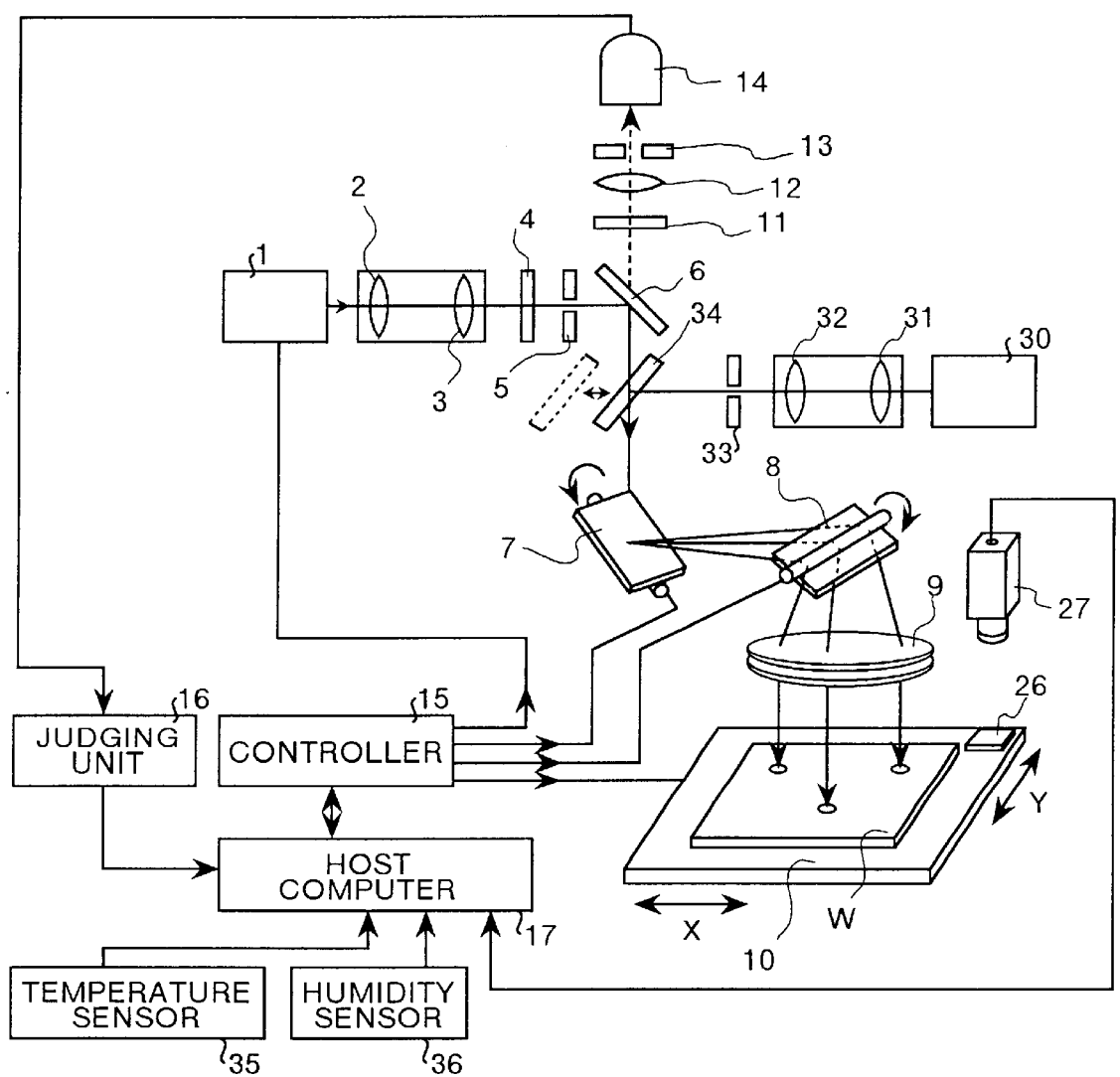
FIG. 20 is a structural diagram showing a seventh embodiment of an apparatus for inspecting a printed circuit board of the invention.

FIG. 20 shows the sixth embodiment of an apparatus for inspecting a printed circuit board of the invention. In FIG. 20, too, same or similar components as shown in FIG. 1 and FIG. 16 are identified with same reference numerals as shown in FIG. 1 and FIG. 16, and their explanation is omitted.

In this embodiment, the re-processing system for re-removing the unremoved material is added. The re-processing system comprises a laser oscillator for re-processing 30, a collimation lens 31, a transfer optical system 32, and a mask plate 33, and a laser optical path selector 34 is selectively assembled in the laser optical path for the galvanomirror. The laser oscillator for re-processing 30 is a laser for resin processing, which may be carbon dioxide laser or solid laser.

While inspecting the printed circuit board W by the laser oscillator 1 for inspection, when a defect is judged at a certain stop hole, the laser optical path selector 34 is inserted into the laser optical path, and laser beam is emitted from the laser oscillator for re-processing 30.

The optical axes of the laser beam from the laser oscillator 1 for inspection and the laser beam of the laser oscillator for re-processing 30 are mutually superposed, and emitted to a same point on the printed circuit board W, the printed circuit board W is processed and the unremoved material is removed again.

After this processing, the laser optical path selector 34 is removed from the laser optical path, and the stop hole is inspected again by the laser beam from the laser oscillator 1 for inspection, and when approved, the next position is inspected.

Thus, since the defective part can be corrected on the inspection apparatus, the yield is improved.

In this explanation, right after detection of defective part, it is re-processed by using the laser oscillator for re-processing 30, but after inspecting all points of one printed circuit board W, defective positions may be stored in the host computer 17, and after completion of inspection of one printed circuit board W, the laser oscillator for re-processing 30 may be changed over and used for processing the stored defective parts, and same effects are expected by such re-processing.

In our experiments, when the laser beam of 473 nm, 30 nW used in fluorescence detection is focused to a spot size of focal point of about ø1 μm, it is found that the resin can be processed. Accordingly, by adjusting the collimator lens 2 and increasing the scan lens incident diameter, the beam diameter in the resin part is smaller, so that it can be processed. In this state, fluorescence inspection cannot be done, and therefore at the time of fluorescence inspection, the collimator lens 2 is adjusted, and the beam diameter in the resin part is expanded to more than 10 μm, and inspection is done. By thus adjusting the collimator lens 2, both inspection and re-processing can be done.

Without using two laser oscillators 1, 30, re-processing can be also done only by one laser oscillator 1, and the initial cost is low, and the yield can be improved.

Herein, the beam diameter is 1 μm in processing and about 10 μm in inspection, and this is a case of the laser beam of 473 nm and 30 mW, and by using a larger laser output, of course, the diameter for processing may be larger. It is preferred that the processing beam diameter is larger. For example, when re-processing a stop hole of ø100 μm with 1 μm beam, the galvanomirror must be scanned 100 times, and it takes much time.

In the case of a beam diameter not suited to processing, after processing with carbon dioxide laser, by starting processing from the carbide layer, it is known that processing can be started. Therefore, to shorten the re-processing time, it is effective to increase the beam diameter somewhat, and start processing from the carbide area.

Thus, when the resin itself can be processed, the processed circuit boards for correction may be periodically supplied into the line and processed, and observed by the vision sensor 27, so that the position can be corrected.

If, however, the laser beams from the laser oscillator 1 for inspection and laser oscillator for re-processing 30 are different in wavelength, since the scan lens 9 is also dependent on wavelength, it is necessary to correct separately in both. By this correction, complete superposing of the laser optical axes of the laser oscillator 1 for inspection and laser oscillator for re-processing 30 can be confirmed.

Figure 21:
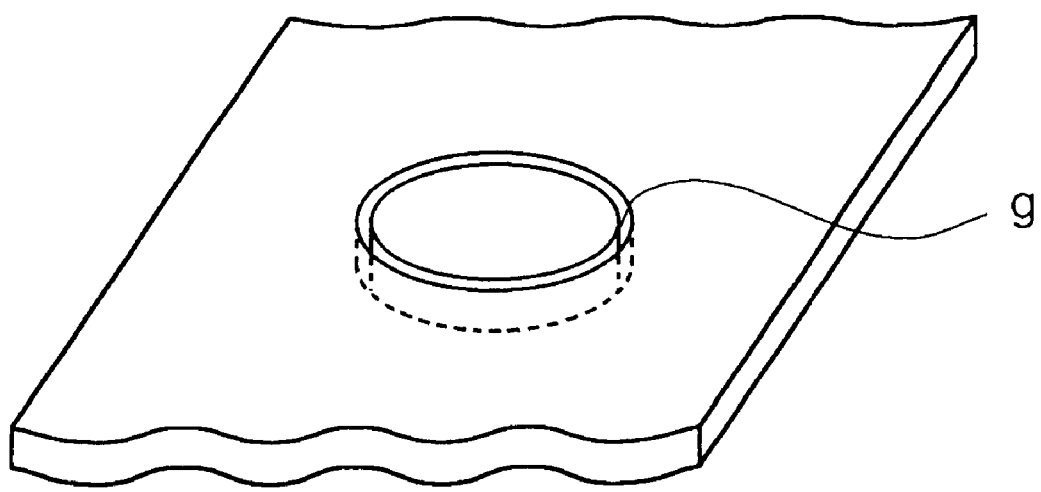
FIGS. 21(a) and (b) are perspective views showing processing pattern for correcting optical distortion.
Figure 21:
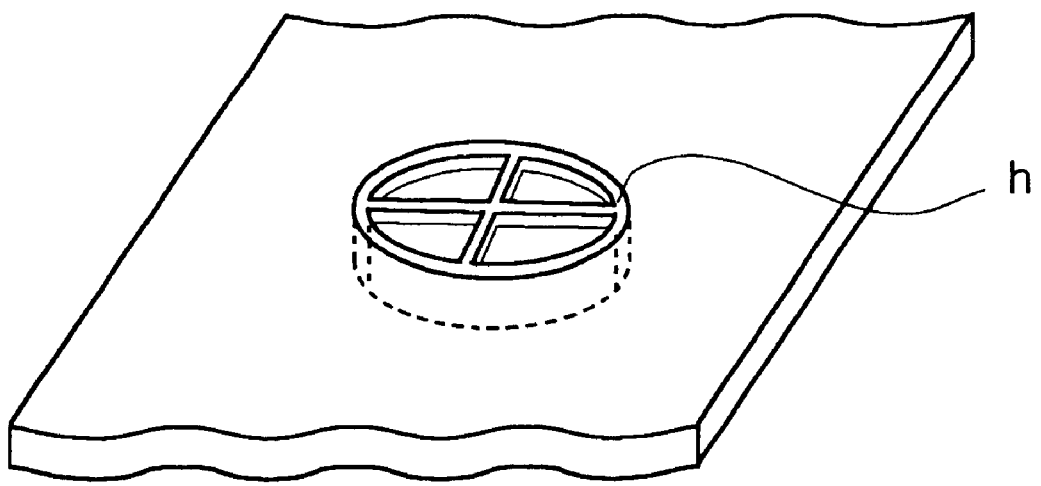
Figure 22:
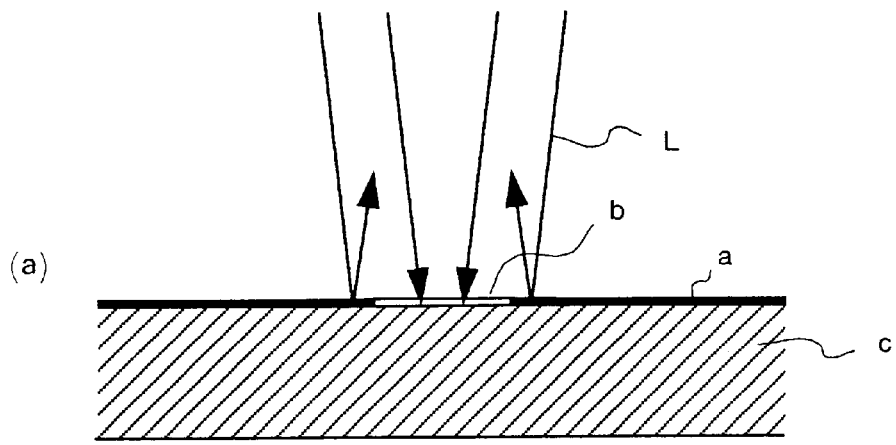
FIG. 22 is an explanatory diagram schematically showing laser processing of printed circuit board.
Figure 23:
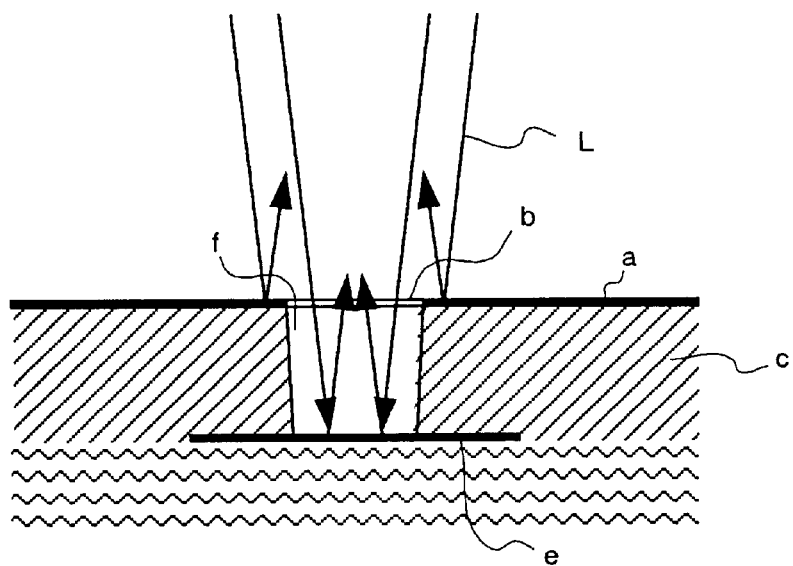
FIG. 23 is an explanatory diagram schematically showing laser processing of stop hole.
Figure 24:
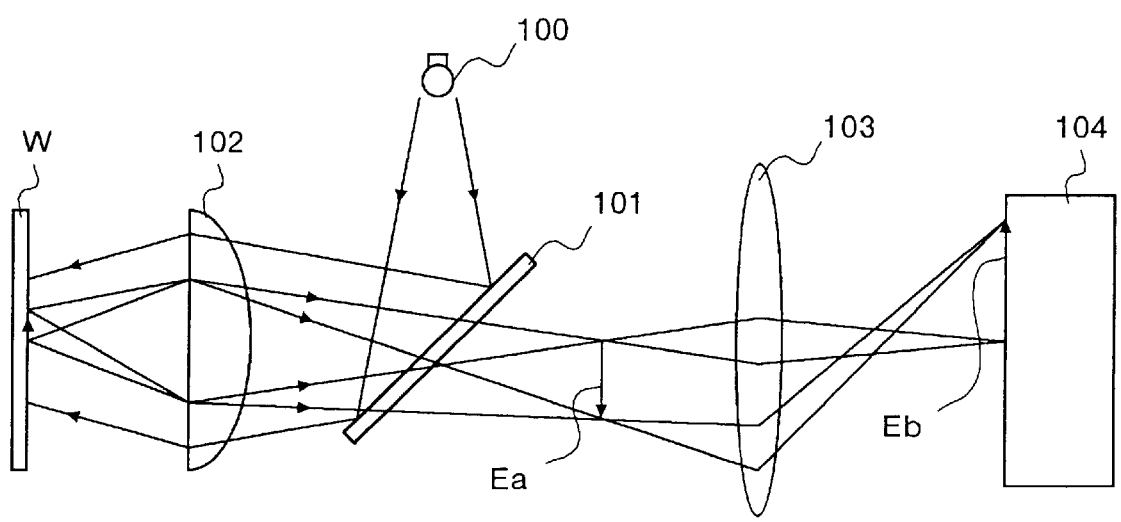
FIG. 24 is a structural diagram showing a conventional apparatus for inspecting a printed circuit board.
Figure 25:
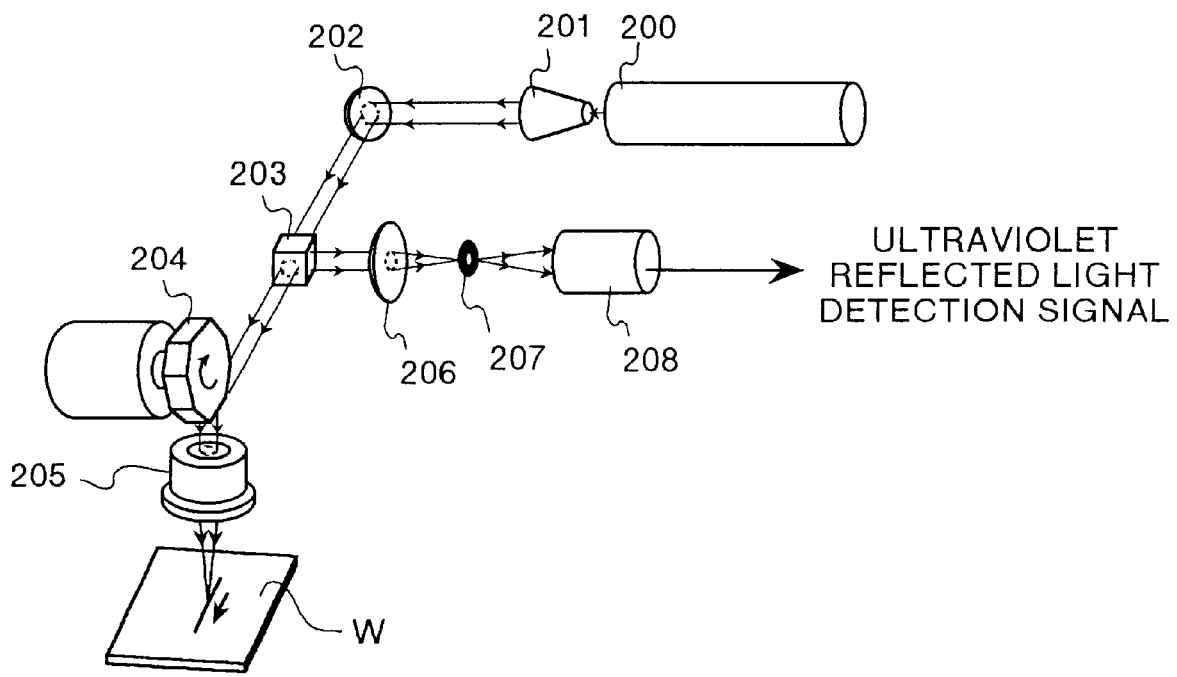
FIG. 25 is a structural diagram showing a conventional apparatus for inspecting a printed circuit board.

If the processing hole is about 1 μm, it cannot be detected by the vision sensor 27 or the like, and as shown in FIGS. 21 (*a*), (*b*), it is easy to judge by drawing a pattern such as ring g or cross h on the circuit board, so that it can discriminated by the vision sensor 27.

INDUSTRIAL APPLICABILITY

As described herein, the apparatus for inspecting a printed circuit board by using laser beam of the invention is suited to optical inspection of blind via hole or groove machined in a laminated printed wiring board.

What is claimed is:

1. An apparatus for inspecting a printed circuit board onto which at least one of a stop hole or a groove is processed, the apparatus comprising:

a laser oscillator;

a scanning device including:

two scanning optical systems scanning within mutually orthogonal planes, and a scan lens, wherein the scanning device positions an irradiation portion of a laser beam emitted from said laser oscillator to a position of arbitrary coordinates in an X-axis direction and a Y-axis direction orthogonal to said X-axis direction;

a detector for detecting a light generated from the printed circuit board irradiated with the laser beam; and a controller storing a position of coordinates of the at least one of the stop hole or the groove in the printed circuit board, and controlling said scanning device to direct the irradiation position of the laser beam to a position corresponding to the stored position of coordinates.

2. The apparatus for inspecting a printed circuit board according to claim 1 further comprising:

a judging unit for judging a quality of an inspection result at each position of coordinates on the basis of an output signal of said detector.

3. The apparatus for inspecting a printed circuit board according to claim 1 further comprising a focusing unit for focusing the laser beam emitted from said laser oscillator; and an image transfer optical system and a mask member disposed between said laser oscillator and said focusing unit.

4. The apparatus for inspecting a printed circuit board according to claim 1, wherein the beam diameter of the laser beam emitted to the printed circuit board to be inspected is set smaller than the diameter of a stop hole or width of a groove.

5. The apparatus for inspecting a printed circuit board according to claim 1, wherein approval or rejection is judged by emitting a spot of laser beam to the plurality of positions of a stop hole or a groove to be inspected.

6. The apparatus for inspecting a printed circuit board according to claim 1, wherein approval or rejection is judged by scanning a stop hole or a groove in a cross form.

7. The apparatus for inspecting a printed circuit board according to claim 1, wherein said detector has optical elements disposed in an array, and is designed to issue signals from each optical element.

8. The apparatus for inspecting a printed circuit board according to claim 1 further comprising, a camera; and a spectroscope disposed on the way of an optical path of reflected light from the printed board for separating the reflected light from the printed circuit board into said detector and said camera.

9. The apparatus for inspecting a printed circuit board according to claim 1 further comprising a light shielding unit for selectively shielding the propagation of the laser beam emitted from said laser oscillator and the reflected light from said printed circuit board.

10. The apparatus for inspecting a printed circuit board according to claim 1, wherein the criterion is set on the basis of the light intensity of the resin part of said printed circuit board to be inspected actually measured before start of inspection, and the light intensity of normal hole.

11. The apparatus for inspecting a printed circuit board according to claim 1, wherein trouble of said laser oscillator or the like is self-diagnosed on the basis of the light intensity of said printed circuit board to be inspected actually measured before start of inspection.

12. The apparatus for inspecting a printed circuit board according to claim 1 further comprising a laser detector for detecting the intensity of the laser beam emitted from the laser oscillator, wherein approval or rejection is judged by the output signal of said detector and output signal of said laser detector.

13. The apparatus for inspecting a printed circuit board according to claim 1, wherein a test piece is fixed at a specified position, and a laser beam is emitted to the test piece to detect the irradiation position, and thereby the error of the optical system is corrected.

14. The apparatus for inspecting a printed circuit board according to claim 13 further comprising, a temperature detecting unit; and a humidity detecting unit, wherein the error of the optical system is corrected when the temperature detected by said temperature detecting unit or the humidity detected by said humidity detecting unit crosses a specified value.

15. The apparatus for inspecting a printed circuit board according to claim 13, wherein the error of the optical system is corrected periodically at every specified interval.

16. The apparatus for inspecting a printed circuit board according to claim 1 further comprising, a laser oscillator for re-processing; and a laser optical path selector for emitting the laser beam of said laser oscillator for re-processing selectively to the printed circuit board with the same optical axis as the laser beam of said laser oscillator, wherein the defective part is corrected by emitting the laser beam of said laser oscillator for re-processing to the processing part of the stop hole or the like judged to be defective.

17. The apparatus for inspecting a printed circuit board according to claim 16, wherein the position of coordinates at the location of a defective part is stored, and the defective part is processed after inspection of one printed circuit board.

18. The apparatus for inspecting a printed circuit board according to claim 1 further comprising a collimation mechanism for changing the beam diameter of the laser beam emitted from said laser oscillator, wherein the defective part is corrected by emitting a laser beam of a beam diameter reduced from that of inspection by said collimation mechanism, to the processing part of the stop hole or the like judged to be defective.

19. The apparatus for inspecting a printed circuit board according to claim 18, wherein the defective part is processed, starting from a carbide area near the defective part.

20. The apparatus for inspecting a printed circuit board according to claim 1, wherein a processing substrate for correction is processed, and the error of the optical system is corrected by detecting this processing position.

21. The apparatus for inspecting a printed circuit board according to claim 20, wherein an annular or cross shape is processed, and the error of the optical system is corrected by detecting this processing position.

* * * * *